United States Patent
Moskowitz et al.

(10) Patent No.: US 10,098,678 B2
(45) Date of Patent: *Oct. 16, 2018

(54) BI-DIRECTIONAL FIXATING/LOCKING TRANSVERTEBRAL BODY SCREW/INTERVERTEBRAL CAGE STAND-ALONE CONSTRUCTS WITH VERTICAL HEMI-BRACKET SCREW LOCKING MECHANISM

(71) Applicant: Moskowitz Family LLC, Rockville, MD (US)

(72) Inventors: Nathan C. Moskowitz, Rockville, MD (US); Mosheh T. Moskowitz, Rockville, MD (US); Ahmnon D. Moskowitz, Rockville, MD (US); Pablo A. Valdivia Y Alvarado, Cambridge, MA (US)

(73) Assignee: Moskowitz Family LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/397,198

(22) Filed: Jan. 3, 2017

(65) Prior Publication Data
US 2017/0303979 A1    Oct. 26, 2017

Related U.S. Application Data

(60) Continuation of application No. 13/418,335, filed on Mar. 12, 2012, now Pat. No. 9,532,821, which is a
(Continued)

(51) Int. Cl.
*A61B 17/70*    (2006.01)
*A61B 17/80*    (2006.01)
(Continued)

(52) U.S. Cl.
CPC ...... *A61B 17/8042* (2013.01); *A61B 17/7064* (2013.01); *A61B 17/809* (2013.01);
(Continued)

(58) Field of Classification Search
CPC ............ A61B 17/8042; A61B 17/7064; A61B 17/809; A61B 17/86; A61B 2017/922;
(Continued)

(56) References Cited

U.S. PATENT DOCUMENTS 2,360,942 A    10/1944   Ellerstein
4,064,881 A    12/1977   Meredith
(Continued)

FOREIGN PATENT DOCUMENTS

FR    2727003        5/1996
WO    2004/093749    11/2004
WO    2006/091503    8/2006

OTHER PUBLICATIONS

Dieter Grob et al., "Clinical Experience With the Dynesys Semirigid Fixation System for the Lumbar Spine," SPINE, vol. 30, No. 3, 2005, pp. 324-331.
(Continued)

*Primary Examiner* — Pedro Philogene
(74) *Attorney, Agent, or Firm* — Fish & Richardson P.C.

(57) ABSTRACT

A bi-directional fixating transvertebral (BDFT) screw/cage apparatus is provided. The BDFT apparatus includes an intervertebral cage including a plurality of internal angled screw guides, a plurality of screw members, and a cage indentation adjacent to the screw guides that independently or supplemented by other screw locking mechanisms prevents the screw members from pulling out of the internal angled screw guides. The internal angled screw guides orient a first screw member superiorly and a second screw member inferiorly. The intervertebral cage is adapted for posterior
(Continued)

lumbar intervertebral placement, anterior lumbar intervertebral placement, anterio-lateral thoracic intervertebral placement, or anterior cervical intervertebral placement.

17 Claims, 26 Drawing Sheets

Related U.S. Application Data continuation-in-part of application No. 13/103,994, filed on May 9, 2011, now Pat. No. 9,603,713, which is a division of application No. 12/054,335, filed on Mar. 24, 2008, now Pat. No. 7,972,363, which is a continuation-in-part of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279, said application No. 13/418,335 is a continuation-in-part of application No. 13/084,543, filed on Apr. 11, 2011, now Pat. No. 8,353,913, which is a division of application No. 11/842,855, filed on Aug. 21, 2007, now Pat. No. 7,942,903, said application No. 13/418,335 is a continuation-in-part of application No. 13/401,829, filed on Feb. 21, 2012, now Pat. No. 9,744,052, application No. 15/397,198, which is a continuation of application No. 13/418,323, filed on Mar. 12, 2012, now Pat. No. 9,814,601, which is a continuation-in-part of application No. 13/103,994, filed on May 9, 2011, now Pat. No. 9,603,713, which is a division of application No. 12/054,335, filed on Mar. 24, 2008, now Pat. No. 7,972,363, which is a continuation-in-part of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279, said application No. 13/418,323 is a continuation-in-part of application No. 13/401,829, filed on Feb. 21, 2012, now Pat. No. 9,744,052, application No. 15/397,198, which is a continuation-in-part of application No. 13/401,829, filed on Feb. 21, 2012, now Pat. No. 9,744,052, which is a continuation-in-part of application No. 13/103,994, filed on May 9, 2011, now Pat. No. 9,603,713, which is a division of application No. 12/054,335, filed on Mar. 24, 2008, now Pat. No. 7,792,363, which is a continuation of application No. 11/842,855, filed on Aug. 21, 2007, now Pat. No. 7,942,903, which is a continuation of application No. 11/536,815, filed on Sep. 29, 2006, now Pat. No. 7,846,188, which is a continuation-in-part of application No. 11/208,644, filed on Aug. 23, 2005, now Pat. No. 7,704,279, said application No. 13/401,829 is a continuation-in-part of application No. 13/084,543, filed on Apr. 11, 2011, now Pat. No. 8,353,913, which is a division of application No. 11/842,855, filed on Aug. 21, 2007, now Pat. No. 7,942,903.

(60) Provisional application No. 61/451,582, filed on Mar. 10, 2011, provisional application No. 61/451,579, filed on Mar. 10, 2011, provisional application No. 61/445,034, filed on Feb. 21, 2011, provisional application No. 60/670,231, filed on Apr. 12, 2005.

(51) Int. Cl.
    *A61B 17/86*     (2006.01)
    *A61B 17/92*     (2006.01)
    *A61F 2/28*     (2006.01)
    *A61F 2/30*     (2006.01)
    *A61F 2/44*     (2006.01)

(52) U.S. Cl.
    CPC ............. *A61F 2/447* (2013.01); *A61B 17/86* (2013.01); *A61B 2017/922* (2013.01); *A61F 2002/2835* (2013.01); *A61F 2002/30476* (2013.01); *A61F 2002/30772* (2013.01); *A61F 2002/30787* (2013.01); *A61F 2002/448* (2013.01); *A61F 2002/4475* (2013.01); *A61F 2220/0025* (2013.01)

(58) Field of Classification Search
    CPC ............... A61F 2/44; A61F 2002/2835; A61F 2002/30476; A61F 2002/30772; A61F 2002/30787; A61F 2002/4475; A61F 2002/448; A61F 2220/0025
    USPC ..................... 606/246–279, 300–328, 72; 623/17.11–17.16
    See application file for complete search history.

(56) References Cited

U.S. PATENT DOCUMENTS

| | | |
|---|---|---|
| 4,554,914 A | 11/1985 | Kapp et al. |
| 4,599,086 A | 7/1986 | Doty |
| 4,636,217 A | 1/1987 | Ogilvie et al. |
| 4,904,261 A | 2/1990 | Dove et al. |
| 4,960,420 A | 10/1990 | Goble et al. |
| 4,997,432 A | 3/1991 | Keller |
| 5,005,749 A | 4/1991 | Aranyi |
| 5,062,850 A | 11/1991 | MacMillan |
| 5,123,926 A | 6/1992 | Pisharodi |
| 5,290,312 A | 3/1994 | Kojimoto et al. |
| 5,405,391 A | 4/1995 | Henderson et al. |
| 5,413,583 A | 5/1995 | Wohlers |
| 5,454,819 A | 10/1995 | Knoepfler |
| 5,514,180 A | 5/1996 | Heggeness et al. |
| 5,660,188 A | 8/1997 | Groiso |
| 5,667,472 A | 9/1997 | Finn et al. |
| 5,713,912 A | 2/1998 | Porter |
| 5,782,832 A | 7/1998 | Larsen et al. |
| 5,865,848 A | 2/1999 | Baker |
| 5,888,223 A | 3/1999 | Bray, Jr. |
| 5,916,224 A | 6/1999 | Esplin |
| 5,951,574 A | 9/1999 | Stefanchik et al. |
| 5,960,522 A | 10/1999 | Boe |
| 5,968,054 A | 10/1999 | Yeatts et al. |
| 5,976,136 A | 11/1999 | Bailey et al. |
| 6,126,689 A | 10/2000 | Brett |
| 6,224,602 B1 | 5/2001 | Hayes |
| 6,235,034 B1 | 5/2001 | Bray |
| 6,322,562 B1 | 11/2001 | Wolter |
| 6,342,074 B1 | 1/2002 | Simpson |
| 6,368,350 B1 | 4/2002 | Erickson et al. |
| 6,375,682 B1 | 4/2002 | Fleischmann et al. |
| 6,419,704 B1 | 7/2002 | Ferree |
| 6,432,106 B1 | 8/2002 | Fraser |
| 6,454,807 B1 | 9/2002 | Jackson |
| 6,458,159 B1 | 10/2002 | Thalgott |
| 6,527,804 B1 | 3/2003 | Gauchet et al. |
| 6,533,818 B1 | 3/2003 | Weber et al. |
| 6,558,423 B1 | 5/2003 | Michelson |
| 6,572,653 B1 | 6/2003 | Simonson |
| 6,579,318 B2 | 6/2003 | Varga et al. |
| 6,582,468 B1 | 6/2003 | Gauchet |

(56) References Cited

U.S. PATENT DOCUMENTS

| | | |
|---|---|---|
| 6,613,055 B2 | 9/2003 | Di Emidio |
| 6,629,998 B1 | 10/2003 | Lin |
| 6,641,614 B1 | 11/2003 | Wagner et al. |
| 6,655,243 B2 | 12/2003 | Anderson et al. |
| 6,716,247 B2 | 4/2004 | Michelson |
| 6,719,794 B2 | 4/2004 | Gerber |
| 6,723,126 B1 | 4/2004 | Berry |
| 6,733,532 B1 | 5/2004 | Gauchet et al. |
| 6,764,491 B2 | 7/2004 | Frey et al. |
| 6,770,094 B2 | 8/2004 | Fehling et al. |
| 6,824,564 B2 | 11/2004 | Crozet |
| 6,852,117 B2 | 2/2005 | Orlowski |
| 6,890,355 B2 | 5/2005 | Michelson |
| 6,904,308 B2 | 6/2005 | Frisch et al. |
| 6,953,477 B2 | 10/2005 | Berry |
| 6,955,671 B2 | 10/2005 | Uchikubo |
| 6,962,606 B2 | 11/2005 | Michelson |
| 6,972,019 B2 | 12/2005 | Michelson |
| 6,974,480 B2 | 12/2005 | Messerli et al. |
| 7,030,904 B2 | 4/2006 | Adair et al. |
| 7,033,394 B2 | 4/2006 | Michelson |
| 7,037,258 B2 | 5/2006 | Chatenever et al. |
| 7,077,864 B2 | 7/2006 | Byrd et al. |
| 7,097,615 B2 | 8/2006 | Banik et al. |
| 7,135,043 B2 | 11/2006 | Nakahara et al. |
| 7,211,112 B2 | 5/2007 | Baynham et al. |
| 7,232,464 B2 | 6/2007 | Mathieu et al. |
| 7,238,203 B2 | 7/2007 | Bagga et al. |
| 7,326,248 B2 | 2/2008 | Michelson |
| 7,442,209 B2 * | 10/2008 | Michelson ............ A61F 2/4455 623/17.11 |
| 7,442,299 B2 | 10/2008 | Lee et al. |
| 7,615,059 B2 | 11/2009 | Watschke et al. |
| 7,618,456 B2 | 11/2009 | Mathieu et al. |
| 7,628,816 B2 | 12/2009 | Magerl et al. |
| 7,704,279 B2 | 4/2010 | Moskowitz et al. |
| 7,727,246 B2 | 6/2010 | Sixto et al. |
| 7,776,047 B2 | 8/2010 | Fanger et al. |
| 7,776,093 B2 | 8/2010 | Wolek et al. |
| 7,803,162 B2 | 9/2010 | Marnay |
| 7,846,207 B2 | 12/2010 | Lechmann et al. |
| 7,862,616 B2 | 1/2011 | Lechmann et al. |
| 7,875,076 B2 | 1/2011 | Mathieu et al. |
| 7,887,591 B2 | 2/2011 | Aebi et al. |
| 7,942,903 B2 | 5/2011 | Moskowitz et al. |
| 7,959,675 B2 | 6/2011 | Gately |
| 7,972,363 B2 | 7/2011 | Moskowitz et al. |
| 7,985,255 B2 | 7/2011 | Bray et al. |
| 8,029,512 B2 | 10/2011 | Paltzer |
| 8,034,060 B2 | 10/2011 | Keren et al. |
| 8,105,367 B2 | 1/2012 | Austin et al. |
| 8,114,162 B1 | 2/2012 | Bradley |
| 8,137,405 B2 | 3/2012 | Kostuik et al. |
| 8,167,949 B2 | 5/2012 | Tyber et al. |
| 8,268,000 B2 | 9/2012 | Waugh et al. |
| 8,273,127 B2 | 9/2012 | Jones et al. |
| 8,328,872 B2 | 12/2012 | Duffield et al. |
| 8,353,913 B2 | 1/2013 | Moskowitz et al. |
| 8,403,986 B2 | 3/2013 | Michelson |
| 8,414,651 B2 | 4/2013 | Tyber et al. |
| 8,419,797 B2 | 4/2013 | Biedermann et al. |
| 8,425,607 B2 | 4/2013 | Waugh et al. |
| 8,540,774 B2 | 9/2013 | Kueenzi et al. |
| 8,613,761 B2 * | 12/2013 | Lindemann ........ A61B 17/7059 606/289 |
| 8,728,165 B2 | 5/2014 | Parry |
| 9,532,821 B2 * | 1/2017 | Moskowitz ........ A61B 17/7064 |
| 2002/0068977 A1 | 6/2002 | Jackson |
| 2002/0143338 A1 | 10/2002 | Orbay et al. |
| 2003/0130737 A1 | 7/2003 | McGahan et al. |
| 2004/0088054 A1 | 5/2004 | Berry |
| 2004/0177531 A1 | 9/2004 | DiBenedetto et al. |
| 2004/0186569 A1 | 9/2004 | Berry |
| 2004/0193272 A1 * | 9/2004 | Zubok ................ A61B 17/8042 623/17.11 |
| 2004/0220571 A1 | 11/2004 | Assaker et al. |
| 2004/0254644 A1 | 12/2004 | Taylor |
| 2005/0027362 A1 | 2/2005 | Williams et al. |
| 2005/0049590 A1 | 3/2005 | Alleyne et al. |
| 2005/0177235 A1 | 8/2005 | Baynham et al. |
| 2005/0216084 A1 | 9/2005 | Fleischmann |
| 2005/0256576 A1 | 11/2005 | Moskowitz et al. |
| 2005/0261769 A1 | 11/2005 | Moskowitz et al. |
| 2005/0273170 A1 | 12/2005 | Navarro et al. |
| 2005/0278026 A1 | 12/2005 | Gordon et al. |
| 2006/0155285 A1 | 7/2006 | Anderson |
| 2006/0241621 A1 | 10/2006 | Moskowitz et al. |
| 2007/0049943 A1 | 3/2007 | Moskowitz et al. |
| 2007/0167678 A1 | 7/2007 | Moskowitz et al. |
| 2007/0198089 A1 | 8/2007 | Moskowitz et al. |
| 2007/0213820 A1 | 9/2007 | Magerl et al. |
| 2007/0250167 A1 | 10/2007 | Bray et al. |
| 2007/0250172 A1 | 10/2007 | Moskowitz et al. |
| 2007/0276498 A1 | 11/2007 | Aebi et al. |
| 2008/0033440 A1 | 2/2008 | Moskowitz et al. |
| 2008/0177307 A1 | 7/2008 | Moskowitz et al. |
| 2008/0183293 A1 | 7/2008 | Parry et al. |
| 2008/0249569 A1 * | 10/2008 | Waugh ................ A61F 2/30721 606/249 |
| 2008/0249575 A1 | 10/2008 | Waugh et al. |
| 2008/0249625 A1 | 10/2008 | Waugh et al. |
| 2008/0281424 A1 | 11/2008 | Parry et al. |
| 2008/0281425 A1 | 11/2008 | Thalgott et al. |
| 2009/0030520 A1 | 1/2009 | Biedermann et al. |
| 2009/0080997 A1 | 3/2009 | Johnson |
| 2009/0105830 A1 * | 4/2009 | Jones .................... A61F 2/4455 623/17.16 |
| 2009/0105831 A1 | 4/2009 | Jones et al. |
| 2009/0112271 A1 | 4/2009 | Moskowitz et al. |
| 2009/0182430 A1 | 7/2009 | Tyber et al. |
| 2009/0187218 A1 | 7/2009 | Schaffhausen |
| 2009/0210062 A1 | 8/2009 | Thalgott et al. |
| 2009/0224023 A1 | 9/2009 | Moskowitz et al. |
| 2009/0234455 A1 | 9/2009 | Moskowitz et al. |
| 2010/0145460 A1 | 6/2010 | McDonough et al. |
| 2010/0305704 A1 | 12/2010 | Messerli et al. |
| 2010/0324606 A1 | 12/2010 | Moskowitz et al. |
| 2011/0125269 A1 | 5/2011 | Moskowitz et al. |
| 2011/0137349 A1 | 6/2011 | Moskowitz et al. |
| 2011/0178600 A1 | 7/2011 | Moskowitz et al. |
| 2011/0208312 A1 | 8/2011 | Moskowitz et al. |
| 2011/0288646 A1 | 11/2011 | Moskowitz et al. |
| 2011/0295327 A1 | 12/2011 | Moskowitz et al. |
| 2011/0295371 A1 | 12/2011 | Moskowitz et al. |
| 2011/0307011 A1 | 12/2011 | Moskowitz et al. |
| 2011/0319935 A1 | 12/2011 | Moskowitz et al. |
| 2012/0010714 A1 | 1/2012 | Moskowitz et al. |
| 2012/0271423 A1 | 10/2012 | Wallenstein et al. |
| 2012/0277870 A1 | 11/2012 | Wolters et al. |
| 2012/0323330 A1 | 12/2012 | Kueenzi et al. |
| 2012/0330419 A1 | 12/2012 | Moskowitz et al. |
| 2013/0018468 A1 | 1/2013 | Moskowitz et al. |
| 2013/0018469 A1 | 1/2013 | Moskowitz et al. |
| 2013/0018470 A1 | 1/2013 | Moskowitz et al. |
| 2013/0023991 A1 | 1/2013 | Moskowitz et al. |
| 2013/0023992 A1 | 1/2013 | Moskowitz et al. |
| 2013/0053962 A1 | 2/2013 | Moskowitz et al. |
| 2013/0060339 A1 | 3/2013 | Duffield et al. |
| 2013/0073044 A1 * | 3/2013 | Gamache ................ A61F 2/442 623/17.16 |
| 2013/0173002 A1 | 7/2013 | Moskowitz et al. |
| 2013/0282017 A1 | 10/2013 | Moskowitz et al. |
| 2014/0249629 A1 | 9/2014 | Moskowitz et al. |
| 2015/0025637 A1 | 1/2015 | Moskowitz et al. |
| 2015/0105824 A1 | 4/2015 | Moskowitz et al. |
| 2015/0148847 A1 | 5/2015 | Moskowitz et al. |
| 2016/0374830 A1 | 12/2016 | Moskowitz et al. |
| 2017/0252178 A1 | 9/2017 | Moskowitz et al. |

OTHER PUBLICATIONS

Vincent C. Traynelis, "Prosthetics and Biologics: The Wave of the Future," Clinical Neurosurgery, vol. 50, Proceedings of the Con-

(56) References Cited

OTHER PUBLICATIONS gress of Neurological Surgeons, Philadelphia, PA 2002, Chapter 9, pp. 207-219.

E.K. Wai et al., "Disk Replacement Arthroplasties: Can the Success of Hip and Knee Replacements be Repeated in the Spine?," Seminars in Spine Surgery, vol. 15, No. 4 (Dec. 2003), pp. 473-482.

Richard D. Guyer et al.. "Intervertebral Disc Prostheses." Spine Journal. vol. 28. No. 15S. Supp. to Aug. 1, 2003. pp. S15-S23.

International Search Report (ISR) and Written Opinion of the International Searching Authority. dated Dec. 3, 2007, International Application No. PCT/US 07/05005.

International Search Report (ISR) and Written Opinion of the International Searching Authority, dated Jul. 9, 2008, International Application No. PCT/US2007/021013.

International Search Report (ISR) and Written Opinion of the International Searching Authority, dated May 21, 2008, International Application No. PCT/US2007/021015.

\* cited by examiner

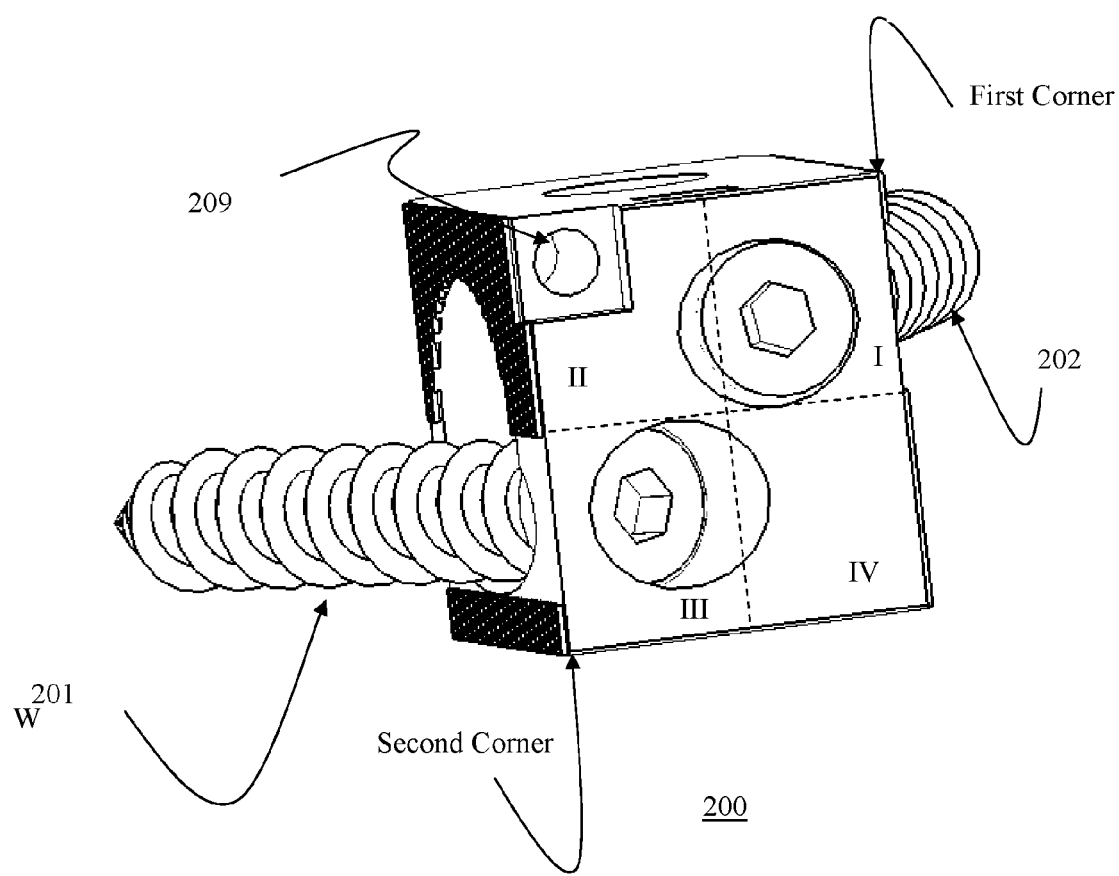
Fig. 6C(ii)

ns and muscle retraction,
BI-DIRECTIONAL FIXATING/LOCKING TRANSVERTEBRAL BODY SCREW/INTERVERTEBRAL CAGE STAND-ALONE CONSTRUCTS WITH VERTICAL HEMI-BRACKET SCREW LOCKING MECHANISM This application is a Continuation application, for which priority is claimed under 35 U.S.C. § 120, U.S. patent application Ser. No. 13/418,225, filed on Mar. 12, 2012, which is a Continuation-In-Part application, for which priority is claimed under 35 U.S.C. § 120, U.S. patent application Ser. No. 13/401,829, filed Feb. 21, 2012, Ser. No. 13/103,994, filed May 9, 2011, Ser. No. 13/084,543, filed Apr. 11, 2011, now U.S. Pat. No. 8,353,913, issued Jan. 15, 2013, Ser. No. 11/842,855, filed Aug. 21, 2007, now U.S. Pat. No. 7,942,903, issued May 17, 2011, Ser. No. 11/536,815, filed Sep. 29, 2006, now U.S. Pat. No. 7,846,188, issued Dec. 7, 2010, and Ser. No. 11/208,644, filed Aug. 23, 2005, now U.S. Pat. No. 7,704,279, issued Apr. 27, 2010, and which is a Divisional application, for which priority is claimed under 35 U.S.C. § 120, U.S. patent application Ser. No. 12/054,335, filed Mar. 24, 2008, now U.S. Pat. No. 7,972,363, issued Jul. 5, 2011, and Ser. No. 11/842,855, filed Aug. 21, 2007, now U.S. Pat. No. 7,942,903, issued May 17, 2011. This application claims the benefit of priority under 35 U.S.C. § 119(e) of U.S. Provisional Application 60/670,231, filed May 12, 2005, 61/451,582, filed Mar. 10, 2011, 61/451,579, filed Mar. 10, 2011, and 61/445,034, filed Feb. 21, 2011.

This application is a Continuation application, for which priority is claimed under 35 U.S.C. § 120, U.S. patent application Ser. No. 13/418,323, filed on Mar. 12, 2012, which is a Continuation-In-Part application, for which priority is claimed under 35 U.S.C. § 120, U.S. patent application Ser. No. 13/401,829, filed Feb. 21, 2012, Ser. No. 13/103,994, filed May 9, 2011, Ser. No. 13/084,543, filed Apr. 11, 2011, now U.S. Pat. No. 8,353,913, issued Jan. 15, 2013, Ser. No. 11/842,855, filed Aug. 21, 2007, now U.S. Pat. No. 7,942,903, issued May 17, 2011, Ser. No. 11/536,815, filed Sep. 29, 2006, now U.S. Pat. No. 7,846,188, issued Dec. 7, 2010, and Ser. No. 11/208,644, filed Aug. 23, 2005, now U.S. Pat. No. 7,704,279, issued Apr. 27, 2010, and which is a Divisional application, for which priority is claimed under 35 U.S.C. § 120, U.S. patent application Ser. No. 12/054,335, filed Mar. 24, 2008, now U.S. Pat. No. 7,972,363, issued Jul. 5, 2011, and Ser. No. 11/842,855, filed Aug. 21, 2007, now U.S. Pat. No. 7,942,903, issued May 17, 2011. This application claims the benefit of priority under 35 U.S.C. § 119(e) of U.S. Provisional Application 60/670,231, filed May 12, 2005, 61/451,582, filed Mar. 10, 2011, 61/451,579, filed Mar. 10, 2011, and 61/445,034, filed Feb. 21, 2011.

This application is a Continuation application, for which priority is claimed under 35 U.S.C. § 120, U.S. patent application Ser. No. 13/401,829, filed on Feb. 21, 2012, which is a Continuation-In-Part application, for which priority is claimed under 35 U.S.C. § 120, U.S. patent application Ser. No. 13/103,994, filed May 9, 2011, Ser. No. 13/084,543, filed Apr. 11, 2011, now U.S. Pat. No. 8,353,913, issued Jan. 15, 2013, Ser. No. 11/842,855, filed Aug. 21, 2007, now U.S. Pat. No. 7,942,903, issued May 17, 2011, Ser. No. 11/536,815, filed Sep. 29, 2006, now U.S. Pat. No. 7,846,188, issued Dec. 7, 2010, and Ser. No. 11/208,644, filed Aug. 23, 2005, now U.S. Pat. No. 7,704,279, issued Apr. 27, 2010, and which is a Divisional application, for which priority is claimed under 35 U.S.C. § 120, U.S. patent application Ser. No. 12/054,335, filed Mar. 24, 2008, now U.S. Pat. No. 7,972,363, issued Jul. 5, 2011, and Ser. No. 11/842,855, filed Aug. 21, 2007, now U.S. Pat. No. 7,942,903, issued May 17, 2011. This application claims the benefit of priority under 35 U.S.C. § 119(e) of U.S. Provisional Application 60/670,231, filed May 12, 2005, 61/451,582, filed Mar. 10, 2011, 61/451,579, filed Mar. 10, 2011, and 61/445,034, filed Feb. 21, 2011.

FIELD OF DISCLOSURE

The present invention relates to a unique universal bi-directional screw (BDS) system, and in particular its application to the spine, also referred to as bi-directional fixating transvertebral (BDFT) screw/cage constructs which can be used as stand-alone intervertebral devices which combine the dual functions of an intervertebral spacer that can be filled with bone fusion material(s), as well as a bi-directional transvertebral bone fixating/fusion screw apparatus. In the posterior lumbosacral and thoracic spine, intervertebral cage/BDFT screw constructs can be used as stand-alone devices obviating the need for pedicle screw fixation in many but not all cases. In the anterior cervical, thoracic and lumbosacral spine, intervertebral cage/BDFT screw constructs can be used as stand-alone devices obviating the need for anterior or lateral (thoracic and lumbosacral) spinal plating, and/or supplemental posterior pedicle screw fixation.

BACKGROUND

The history and evolution of instrumented spinal fusion in the entire human spine has been reviewed in related application Ser. No. 12/054,335, filed on Mar. 24, 2008, Ser. No. 13/084,543, filed on Apr. 11, 2011, Ser. No. 11/842,855, filed on Aug. 21, 2007, Ser. No. 11/536,815, filed on Sep. 29, 2006, and Ser. No. 11/208,644, filed on Aug. 23, 2005, the contents of which are hereby incorporated by reference in their entirety. Conventionally, the majority of posterior cervical and almost all posterior thoracic and lumbosacral fusion surgical techniques are typically supplemented with pedicle screw placement. Conventionally, the majority of anterior cervical spinal fusions, and many anterio-lateral thoracic, and anterior or anterio-lateral lumbosacral fusions are supplemented with anterior or anterior-lateral spinal plating, and very often, in particular in the thoracic and lumbosacral spine, are supplemented with posterior pedicle screw instrumentation.

Complications of pedicle screw placement in cervical, thoracic and lumbosacral spine include duration of procedure, significant tissue dissection and muscle retraction, misplaced screws with neural and/or vascular injury, excessive blood loss, need for transfusions, prolonged recovery, incomplete return to work, and excessive rigidity leading to adjacent segmental disease requiring further fusions and re-operations. Recent advances in pedicle screw fixation including minimally invasive, and stereotactic CT image-guided technology, and the development of flexible rods, imperfectly address some but not all of these issues.

Complications of anterior plating in the cervical spine include potential plate, and/or screw esophageal compression, and misplaced screws leading to neurovascular injury. Complications of anterior or anterior-lateral plating in the anterior lumbar spine include potential devastating injury to the major vessels due to chronic vascular erosion of the major vessels, or acute vascular injuries due to partial or complete plate and/or screw back out. Furthermore, for re-do surgeries, plate removal can be arduous, with potential complications of prolonged esophageal retraction, vascular injury and screw breakage. Recent advances including diminishing the plate width and/or profile, and absorbable plates, imperfectly address some but not all of these issues.

Complications of all conventional spinal anterior intervertebral device constructs are their potential for extrusion in the absence of plating. Hence, they are supplemented with anterior plating to prevent extrusion. Complications of posterior lumbosacral intervertebral device construct in the presence or absence of supplemental pedicle screw fixation is device extrusion, and potential nerve root and/or vascular injuries.

SUMMARY

Herein described are multiple device embodiments which combine in a single stand-alone construct the dual functions of: a) an intervertebral cage spacer which can be filled with bone fusion material maintaining disc height, and, b) a bi-directional fixating/fusion transvertebral body screw apparatus. These embodiments are described for posterior and anterior lumbar (and anterio-lateral thoracic) intervertebral placement, and anterior cervical intervertebral placement. The present invention recognizes the aforementioned problems with prior art apparatus and solves these problems by, among other things, complimenting/improving upon the designs illustrated in the aforementioned related applications. The present application provides an advanced and novel bi-directional fixating transvertebral (BDFT) screw/cage apparatus with a vertical hemi-bracket locking screw mechanism which locks two adjacent screws into position, preventing back out by it's insertion into novel indentations on the upper superior and inferior sides of the screw box which are aligned with the axial midpoint of the upper surface of the cage between two adjacent internalized cage screw guides/screws. These brackets can be easily snapped into the cage indentations and removed by a bracket tool, for example, as described in U.S. Pat. No. 7,942,903, issued on May 17, 2011. This mechanism can be used not only for these constructs but also with any other device which requires a screw locking mechanism, e.g., anterior cervical and lumbar spinal plates, and other orthopedic/medical devices necessitating screw locking mechanisms. The exemplary embodiments improve the probability of a solid fusion.

The exemplary embodiments of a bi-directional fixating transvertebral (BDFT) screw/cage apparatus provide as strong or stronger segmental fusion as pedicle screws without the complications arising from pedicle screw placement, which include misplacement with potential nerve and/or vascular injury, violation of healthy facets, possible pedicle destruction, blood loss, and overly rigid fusions. By placing screws across the intervertebral space from vertebral body to vertebral body, engaging anterior and middle spinal columns and not the vertebral bodies via the transpedicular route thereby excluding the posterior spinal column, then healthy facet joints, if they exist, are preserved. Because the present invention accomplishes both anterior and middle column fusion, without rigidly fixating the posterior column, the present invention in essence creates a flexible fusion.

The present invention recognizes that the very advantage of transpedicular screws which facilitate a strong solid fusion by rigidly engaging all three spinal columns is the same mechanical mechanism whereby complete inflexibility of all columns is incurred thereby leading to increasing rostral and caudal segmental stress which leads to an increased rate of re-operation.

Transvertebral fusion also leads to far less muscle retraction, blood loss and significant reduction in operating room (O.R.) time. Thus, the complication of pedicle screw pull out, and hence, high re-operation rate associated with the current embodiment of flexible fusion pedicle screws/rods is obviated. The lumbosacral intervertebral cage/BDFT screw constructs can be introduced via posterior, lateral, transforaminal or anterior interbody fusion approaches/surgical techniques. Although one can opt to supplement these constructs with transpedicular screws there would be no absolute need for supplemental pedicle screw fixation with these operative techniques.

The anterior placement of a bi-directional fixating transvertebral (BDFT) screw/cage apparatus according to the embodiments of the present invention into the cervical and lumbar spine obviates the need for supplemental anterior cervical or anterior lumbar plating. The sole purpose of these plates is to prevent intervertebral device extrusion. This function is completely obviated and replaced by the dual functioning bi-directional fixating transvertebral (BDFT) screw/cage apparatus, according to the present invention. The obvious advantage of this is a significant savings in operative time, and prevention of injuries associated with plating, in particular esophageal, large and small vessel injuries, and spinal cord nerve root injuries.

Because the embodiments of the bi-directional fixating transvertebral (BDFT) screw/cage apparatus engage a small percentage of the rostral and caudal vertebral body surface area, multi-level fusions can be performed with these devices.

Conventionally, failed anterior lumbar arthroplasties are salvaged by combined anterior and posterior fusions. Intervertebral cage/BDFT screw constructs may be utilized as a one-step salvage mechanism for failed/extruded anteriorly placed lumbar artificial discs obviating the need for supplemental posterior pedicle screws and/or anterior lumbar plating thereby significantly reducing and/or eliminating co-morbidities associated with these other salvage procedures.

Likewise, anterior cervical intervertebral cage/BDFT screw construct placement can be used to salvage failed anterior cervical arthroplasties, and re-do fusions without having to supplement with cervical anterior plates, thereby reducing the morbidity of this procedure.

In addition, if a patient develops a discogenic problem necessitating anterior cervical discectomy and fusion at a level above or below a previously fused and plated segment, the present invention reduces or eliminates the need to remove the prior plate in order to place a new superior plate, because the function of the plate is replaced by the dual functioning intervertebral cervical construct, thereby reducing the operating room time and surgical morbidity of this procedure.

Furthermore, because of the orientation and length of the BDFT screws within the intervertebral cage/BDFT constructs, multiple level fusions can be easily performed.

For example, an exemplary embodiment is directed to an intervertebral cage spacer and bi-directional fixating/fusion transvertebral body screw/cage apparatus. The apparatus can include an intervertebral cage for maintaining disc height. The intervertebral cage may include a first internal screw guide and a second internal screw guide which narrow from top to bottom having an approximate angle of 25 degrees. However, the angles can vary up to forty degrees. The upper superior and inferior walls of the cage bordering the edge of the top of the cage, positioned midway between the two central internal screw guides, have novel indentations for insertion of a vertical screw-locking hemi-bracket. The apparatus may further include a first screw member having a screw with a tapered end and a threaded body disposed within the intervertebral cage, a second screw member with a tapered end and a threaded body disposed within the intervertebral cage, and a vertical hemi-bracket covering the medial-vertical aspect of two adjacent screws which snaps into the indentations of the superior and inferior sides of the cage which are located at a midpoint between the two adjacent internalized screw guides. The locking mechanism may prevent the first screw member and the second screw member from pulling-out of the first internal screw guide and the second internal screw guide. The internal screw guides can be formed to narrow along a length of the screw guide in a direction of descent into the screw guides, thereby providing a preliminary first locking mechanism when the screws engage the screw guides and are countersunk into the top of the cage. The exemplary embodiments of the vertical hemi bracket, which are locked into the cage and cover the screw heads, can provide a secondary additive locking mechanism in combination with the first locking mechanism, thereby definitively preventing screw back out. In other embodiments, only the exemplary embodiments of the vertical hemi bracket, which are locked into the cage and cover the screw heads (or a part of the screw heads), may be provided to function as a primary locking mechanism for definitively preventing screw back out.

Another exemplary embodiment is directed to an integral intervertebral cage spacer and bi-directional fixating/fusion transvertebral body screw apparatus, including an intervertebral cage having a plurality of internal angled screw guides which are inserted into the posterior lumbosacral disc space on either the left or right, or both sides.

In order to achieve screw bone penetration in such a constricted space the internalized screw guides/screw must be located very close to each other and must be obliquely, not horizontally or vertically aligned. The intervertebral cage may include a first internal screw guide and a second internal screw guide which narrow from top to bottom having an approximate angle of twenty five degrees. The angles can vary up to forty degrees. The upper superior and inferior walls of the cage bordering the top of the cage, midway between the two central internal screw guides have novel indentations for insertion of a vertical screw-locking hemi-bracket. The apparatus further includes a first screw member having a screw with a tapered end and a threaded body disposed within the intervertebral cage, a second screw member with a tapered end and a threaded body disposed within the intervertebral cage, and a vertical hemi-bracket covering the medial aspect of two adjacent screws which snaps into the superior and inferior sides of the cage which are located at a midpoint between the two adjacent internalized screw guides. This locking mechanism prevents the first screw member and the second screw member from pulling-out of the first internal screw guide and the second internal screw guide. The internal screw guides can be formed to narrow along a length of the screw guide in a direction of descent into the screw guides, thereby providing a preliminary first locking mechanism when the screws engage the screw guides and are countersunk into the top of the cage. The exemplary embodiments of the vertical hemi bracket, which are locked into the cage and cover the screw heads (or a part of the screw heads), can provide a secondary additive locking mechanism in combination with the first locking mechanism, thereby definitively preventing screw back out. In other embodiments, only the exemplary embodiments of the vertical hemi bracket, which are locked into the cage and cover the screw heads, may be provided to function as a primary locking mechanism for definitively preventing screw back out.

Another exemplary embodiment is directed to a method of inserting a bi-directional fixating transvertebral (BDFT) screw/cage apparatus between a first vertebral body and a second vertebral body. The method can include measuring a dimension of a disc space between the first vertebral body and the second vertebral body, determining that the disc space is a posterior or lateral lumbar disc space, an anterior lumbar disc space, or an anterior cervical disc space, selecting an intervertebral cage based on the measured dimension of the disc space and based on the determination of the disc space being the posterior lumbar disc space, the lateral lumbar disc space, the anterior lumbar disc space, or the anterior cervical disc space, inserting the selected intervertebral cage into a midline of the disc space until the selected intervertebral cage is flush or countersunk relative to the first vertebral body and the second vertebral body, inserting a first screw member into a first internal screw guide of the selected intervertebral cage, inserting a second screw member into a second internal screw guide of the selected intervertebral cage, screwing the first screw member and the second screw member into the first vertebral body and the second vertebral body respectively, confirming a position and placement of the intervertebral cage relative to the first vertebral body and the second vertebral body, and locking the first screw member and the second screw member in a final position by its final turn when it's flush with the surface of the cage. The vertical hemi bracket when inserted and locked into the cage indentations may cover the medial aspects of the screws and therefore may prevent screw back-out when the screws are in their final resting positions.

The posterior lumbar BDFT cage screw apparatus is uniquely designed in order to get into the posterior space and obtain proper screw angulations. Two exemplary embodiments are described; one that is rectangular and one that is elliptical and concave mimicking the posterior intervertebral disc space. In both exemplary embodiments, the axes of the internal screw guides are not horizontally or vertically aligned as they are in the cervical embodiment. Their axes must be oblique one to the other, and the screw guides must be very close to one another in order for the screws to achieve proper angulation, trajectory and vertebral body penetration in such a restricted posterior lumbar inter space.

In the embodiments having an anterior lumbar embodiment four screw design, in order to achieve maximal stability and to prevent subsidence, the lateral two screws penetrate the inferior vertebral body, and the middle two screws project to the superior vertebral body.

In all BDFT embodiments, the screw angle guides have an approximate twenty five degree angle. However, the angles can go up to forty degrees. The angles can be variable or divergent i.e. two adjacent screws can be angled laterally, medially or divergent with respect to each other i.e. one angled laterally and the other angled medially.

In all embodiments the screw drill guide narrows such that the screw head is countersunk into the cage and thus it can be locked even in the absence of an additional screw locking mechanism. The screw locking mechanism described herein is yet an additional mechanism guaranteeing the prevention of screw back out/pull out.

BRIEF DESCRIPTION OF THE DRAWINGS

The accompanying drawings are presented to aid in the description of embodiments of the invention and are provided solely for illustration of the embodiments and not limitation thereof.

DETAILED DESCRIPTION OF THE EXEMPLARY EMBODIMENTS

Aspects of the invention are disclosed in the following description and related drawings directed to specific embodiments of the invention. Alternate embodiments may be devised without departing from the scope of the invention. Additionally, well-known elements of the invention will not be described in detail or will be omitted so as not to obscure the relevant details of the invention.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

With reference to FIGS. 1A-6E, exemplary embodiments of the invention will now be described.

1. Exemplary Medical Device

Referring to FIGS. 1A-6E the above described problems of the conventional art can be solved in the cervical, thoracic and lumbosacral spines by insertion into the denuded intervertebral disc space multiple embodiments of a bi-directional fixating transvertebral (BDFT) screw/cage apparatus.

Figure 1A:
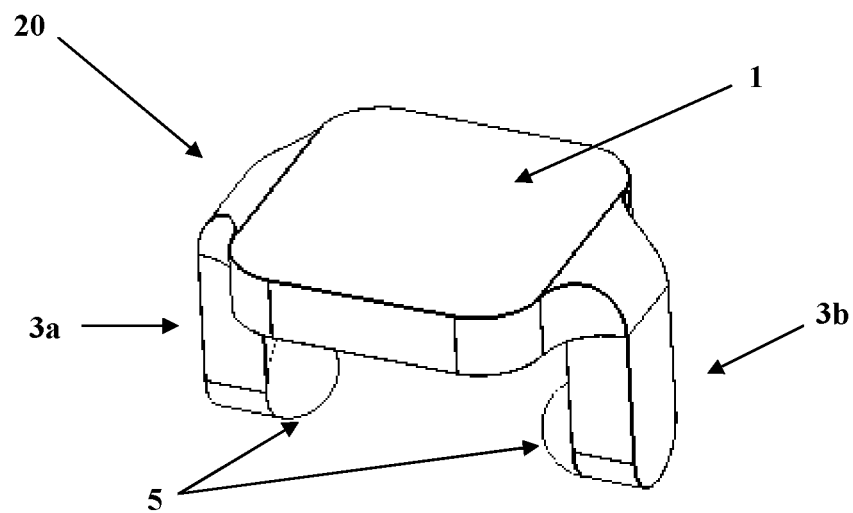
FIG. 1A illustrates a top, perspective (oblique) view of a vertical hemi-bracket screw locking device according to an embodiment of the invention.
Figure 1B:
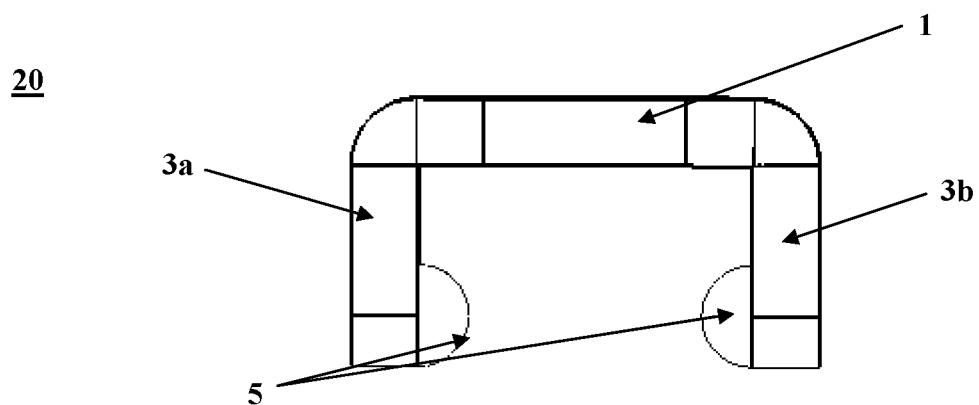
FIG. 1B illustrates a side (anterior-posterior) view of a vertical hemi-bracket screw locking device according to an embodiment of the invention.
Figure 1C:
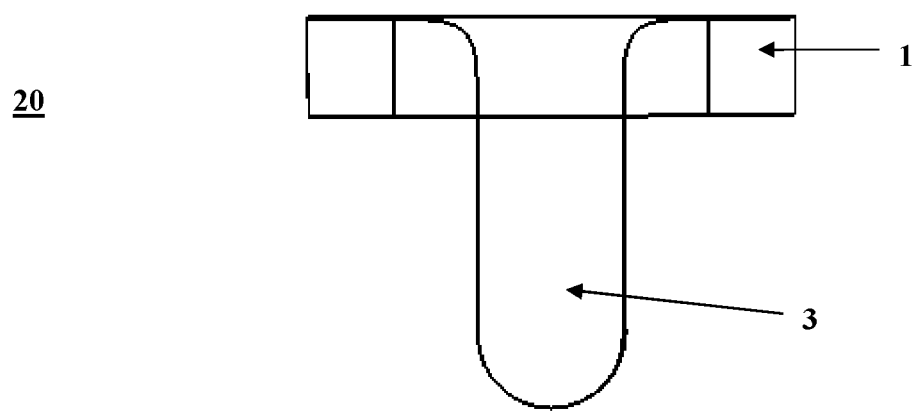
FIG. 1C illustrates a side (lateral) view of a vertical hemi-bracket screw locking device according to an embodiment of the invention.

For example, FIGS. 1A-1C illustrate three-dimensional views of an exemplary embodiment of a vertical hemi-bracket 20. In this embodiment, the bracket 20 drapes over the screw heads (or at least a portion thereof) of screws 30, 40 (FIGS. 2A-5F) and is secured to (e.g., snaps into or onto) a portion of a cage 10, 110, 210 (FIGS. 2A-5F) thereby preventing screws 30, 40 from backing out of the cage 10, 110, 210. The bracket 20 can include a base 1 with arms 3 attached to the base 1. The arms 3a, 3b can extend away from the base 1 such that cage 10, 110, 210 interposes the arm 3a, 3b when the bracket 20 is engaged with the cage 10, 110, 210. In the illustrated exemplary embodiment, the arms 3 can be attached on opposite sides/ends of the base 1. However, in other embodiments, the arms 3 can be attached anywhere along the base 1. The arms 3 can include, for example, a superior arm 3a and an inferior arm 3b (e.g., a first arm and a second arm). In other embodiments, one or more arms can be provided on either side of the base 1. For example, a first arm (e.g., 3a) can extend from a first side of the base 1 and a second arm (e.g., 3b) can extend from a second side (opposite side) of the base 1. In still other embodiments, a number of arms on the first side of the base 1 can be different from a number of arms on the second side of the base 1. For example, two arms can extend from a first side of the base 1 and a single arm can extend from a second side (opposite side) of the base 1, or two arms from a first side of the base 1 and three arms from a second side (opposite side) of the base 1, etc. Other numbers of arms and arrangements are possible within the spirit and scope of the invention.

The superior arm 3a and inferior arm 3b can snap onto or snap-lock into the base 1. The superior arm 3a and inferior arm 3b can be resilient or flexible such that the arms 3a, 3b can be secured to the base 1 by the resilient arms pressing against the sides of the cage 10, 110, 210. The arms 3a, 3b can be secured by frictional forces or by corresponding engaging features formed on a part of the arms 3a, 3b and/or the cage 10, 110, 210.

For example, a portion of the superior arm 3a and inferior arm 3b can snap-lock into indentations 70, 194, 290 of the superior and inferior walls of the cage 10 (FIGS. 2A-5F), respectively. In an exemplary embodiment, each of the superior arm 3a and inferior arm 3b can include a medial protuberance 5 emanating and projecting from an inferior aspect of one or more of the arms 3a, 3b. The protuberances 5 can snap into corresponding cage indentations 70, 194, 290 (FIGS. 2A-5F), thereby locking the bracket 20 on the cage 20, 110, 210 and preventing screws 30, 40 from backing out of the cage 10, 110, 210. In another example, a portion of the superior arm 3a and inferior arm 3b can engage a portion of ridges 50 formed on the superior and inferior surfaces or edges of the lumbar cage 10.

Figure 2A:
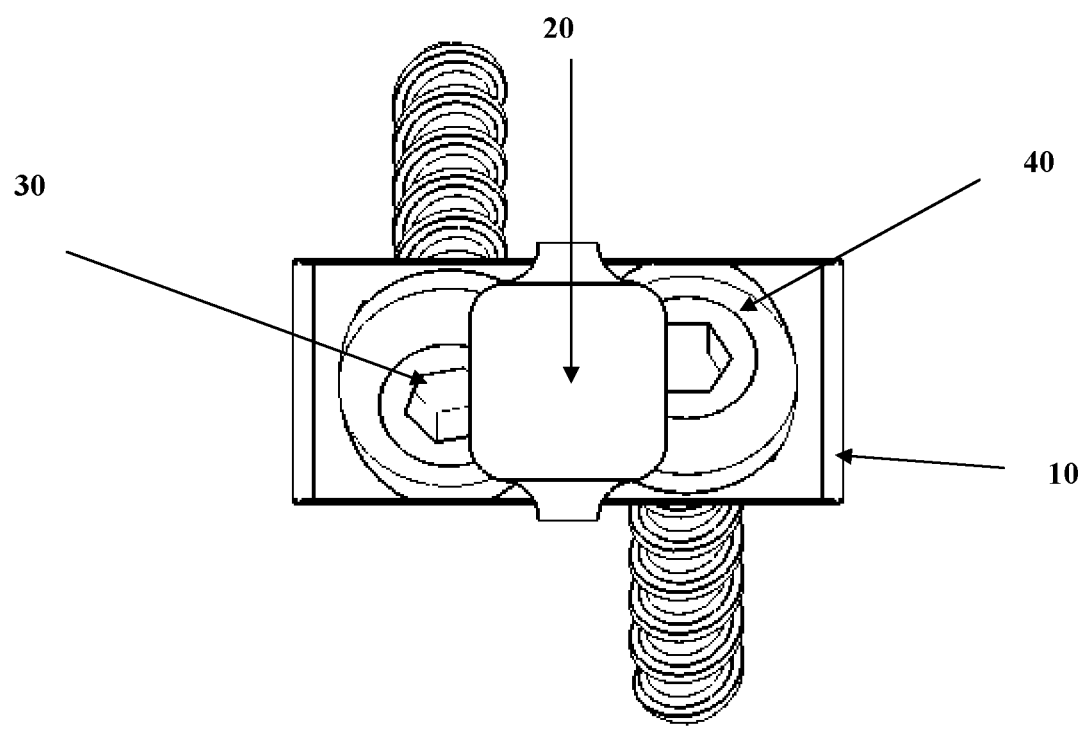
FIG. 2A illustrates a top view of an anterior cervical intervertebral cage/BDFT screw construct according to an embodiment of the invention.
Figure 2B:
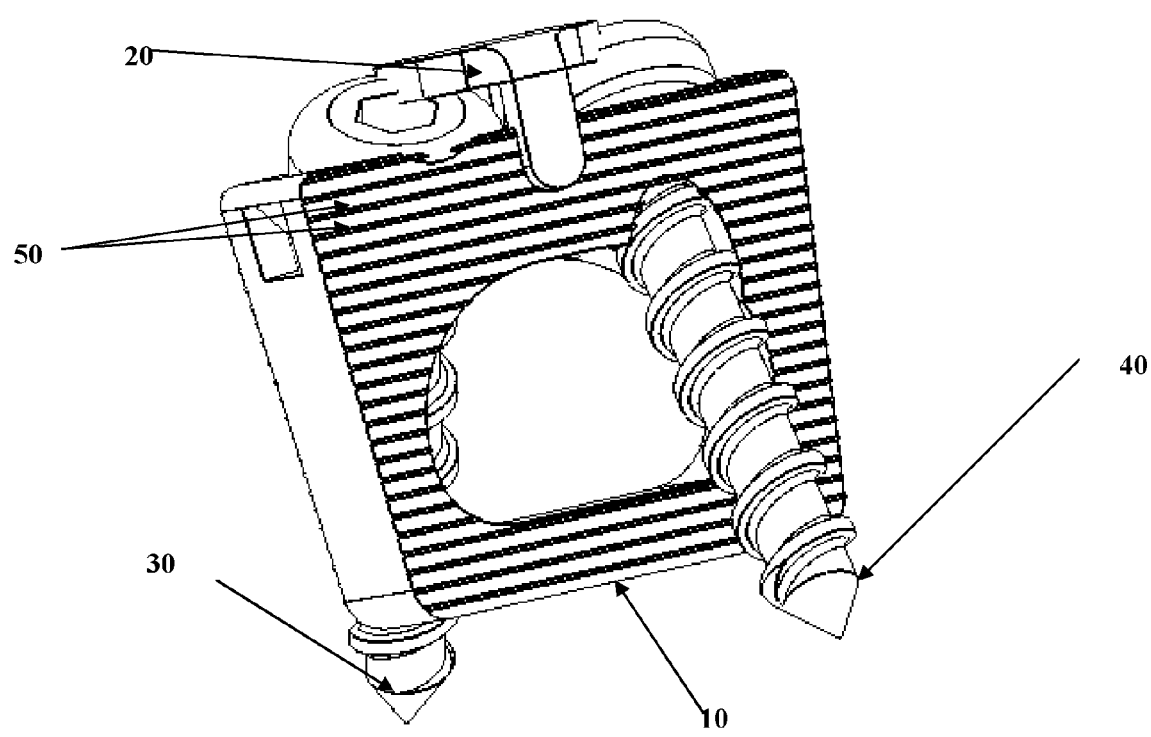
FIG. 2B illustrates a bottom, perspective (bottom isometric) view of an anterior cervical intervertebral cage/BDFT screw construct according to an embodiment of the invention.
Figure 2C:
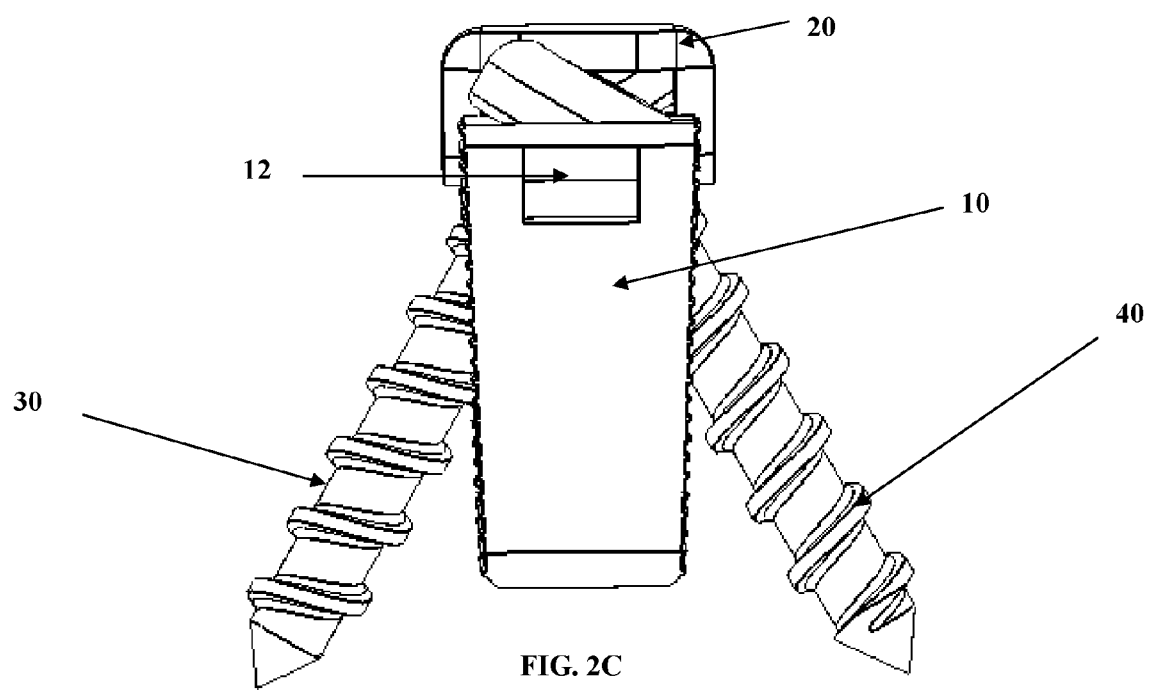
FIG. 2C illustrates a side view of an anterior cervical intervertebral cage/BDFT screw construct according to an embodiment of the invention.
Figure 2D:
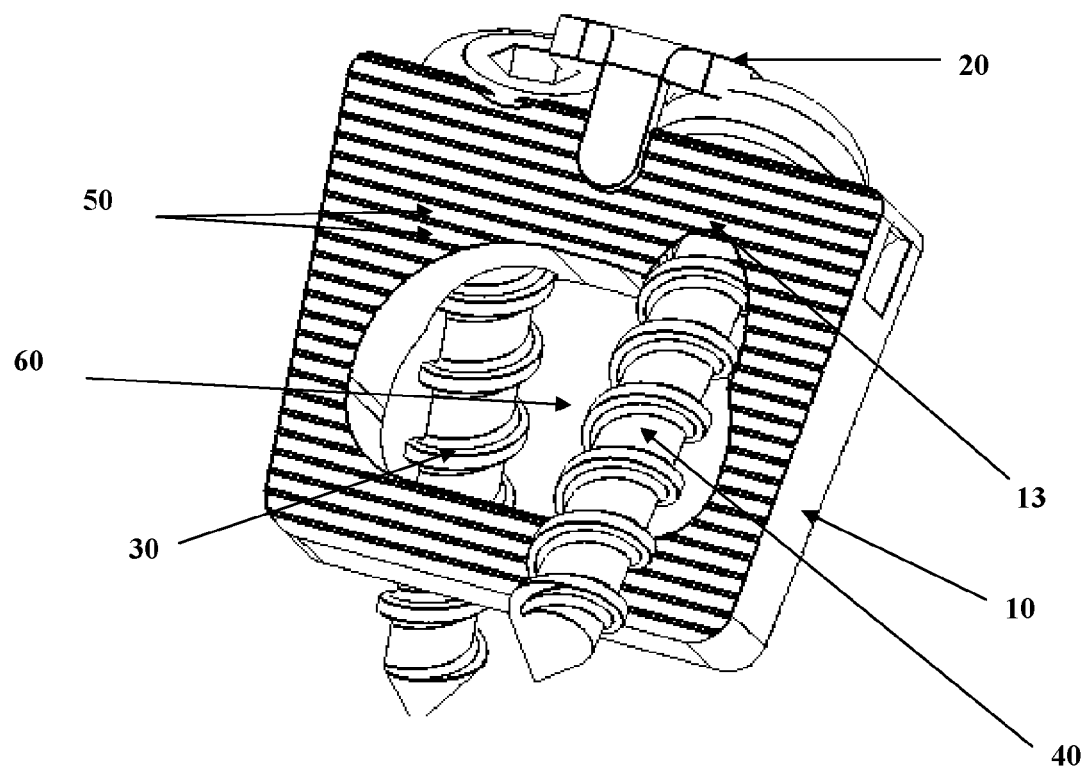
FIG. 2D illustrates a front, perspective (front isometric) view of an anterior cervical intervertebral cage/BDFT screw construct according to an embodiment of the invention.
Figure 2E:
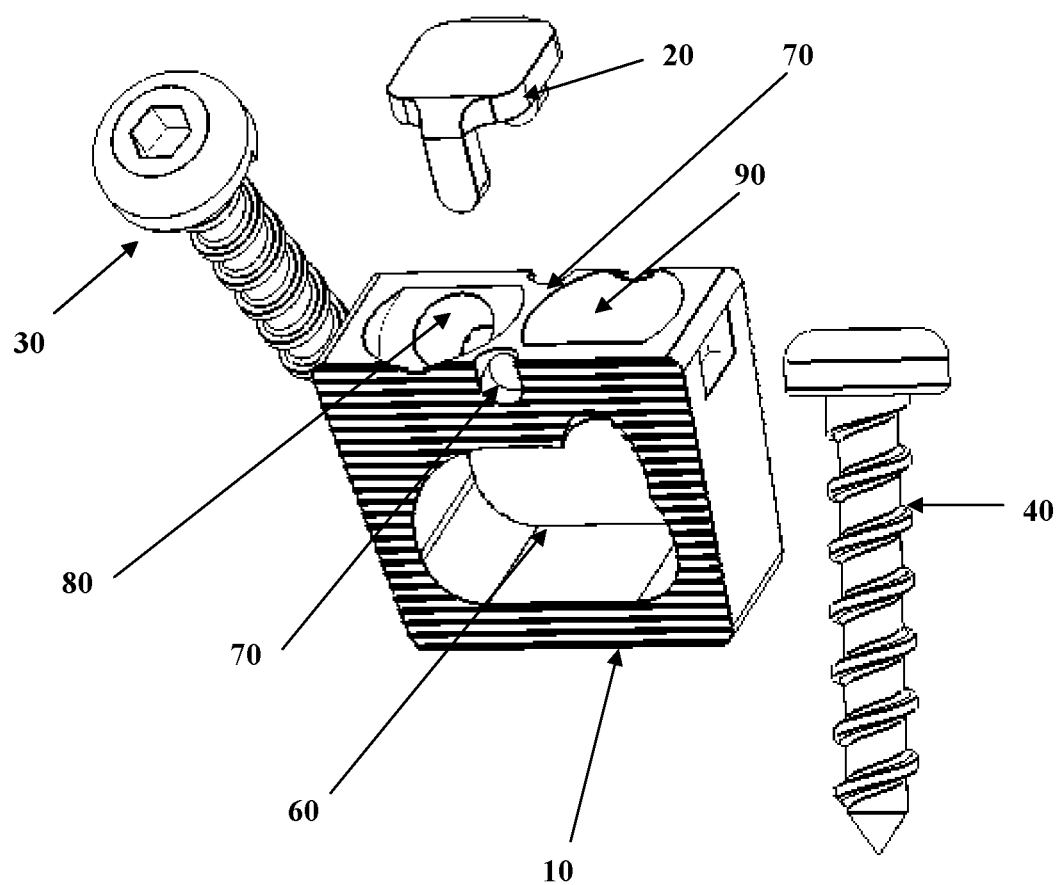
FIG. 2E illustrates a top, perspective, partially exploded (bottom isometric) view of an anterior cervical intervertebral cage/BDFT screw construct according to an embodiment of the invention.
Figure 2F:
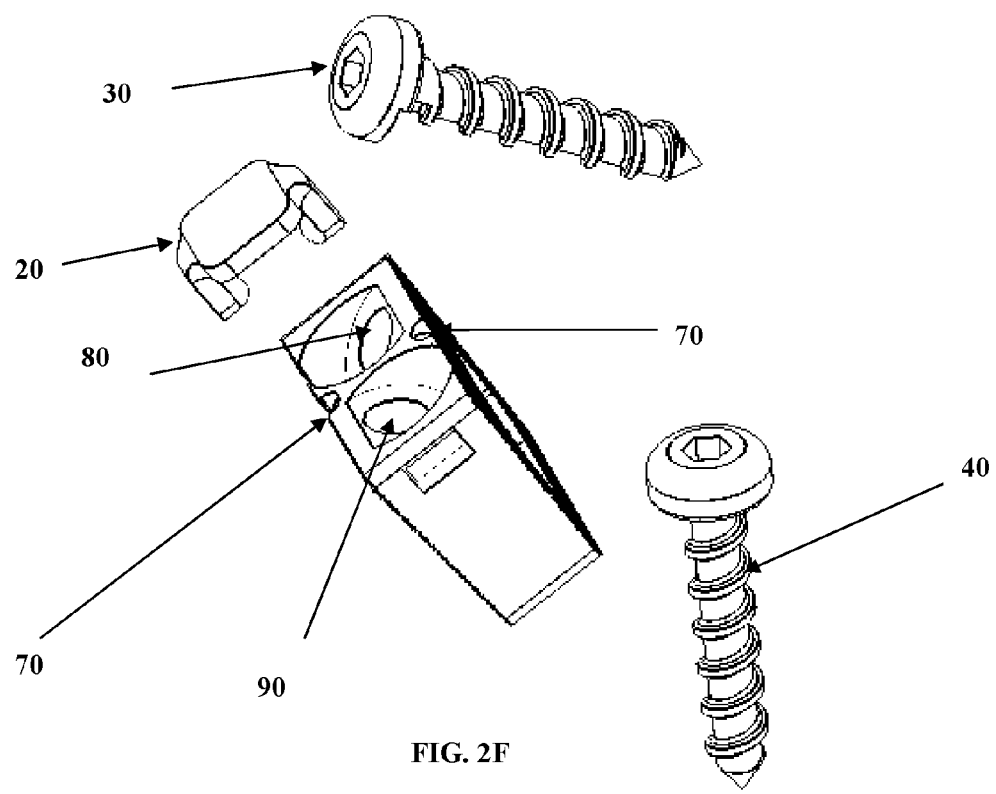
FIG. 2F illustrates a side, perspective, exploded view of an anterior cervical intervertebral cage/BDFT screw construct with internalized angled screw guides according to an embodiment of the invention.
Figure 2G:
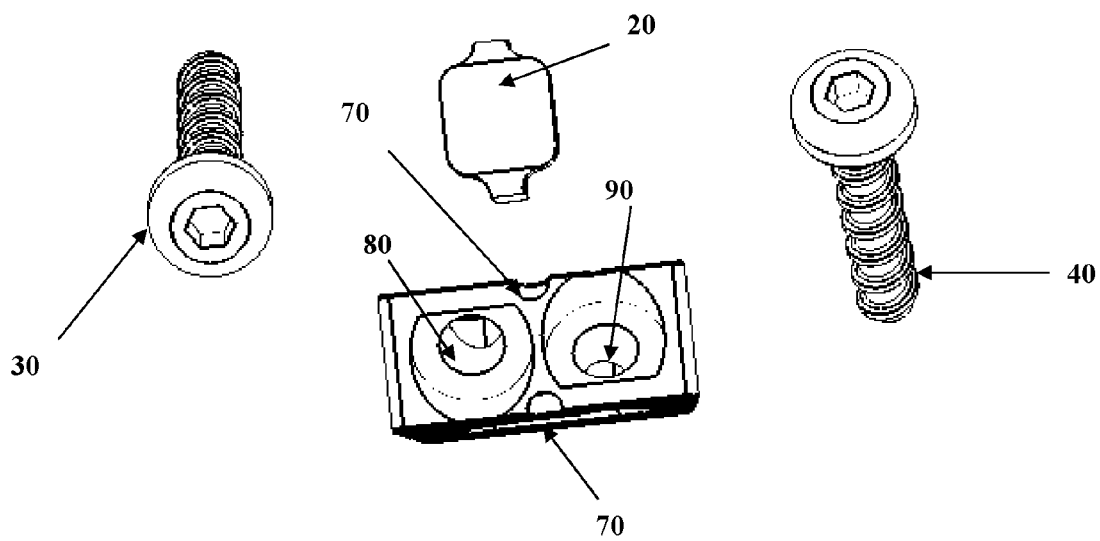
FIG. 2G illustrates a top, perspective, exploded (top isometric) view of an anterior cervical intervertebral cage/BDFT screw construct with visualized internalized angled screw guides according to an embodiment of the invention.

FIGS. 2A-2G illustrate three-dimensional views of an embodiment of an exemplary anterior cervical intervertebral cage/BDFT construct 10. In this embodiment, the top portion of the cage 10 has indentations 70 that are on the upper superior and inferior walls midway between the two internalized screw guides/screws 80, 90 (FIGS. 2E-2G). The vertical hemi bracket 20 snaps into these indentations 70.

The cage 10 also can include indentations or slots 12 on both side surfaces of the cage 10 for insertion of a prong of an implantation tool (see example cage and tool in FIG. 6D; the cage 10 can engage the tool in a similar manner), and more particularly, that engage the distal medial oriented male protuberance of a lateral griper prong of an implantation tool.

In the illustrated embodiment, the indentations 70 are formed on difference side surfaces from the indentations 12, for example, to avoid interference with the insertion tool accessing the indentations 70 of the cage. However, in other embodiments, the indentations 70 and the indentations 12 can be formed on a same side surface. Also, the indentations 70 can be formed at locations other than midway between the screw guides. The indentations 70 can have a variety of shapes and depths. For example, the indentations 70 can have a shape corresponding to a shape of a medial protuberance 5 emanating and projecting from an inferior aspect of one or more of the arms 3a, 3b. In other embodiments, the size and shape of the indentations 70 can be different from the medial protuberance 5 of the arms 3a, 3b.

In an exemplary embodiment, a side surface of the cage 10 can be elliptically contoured when viewed from the side (FIG. 1C) to fit into the bi-concave cervical disc space. The embodiment includes two screws 30, 40. A first screw 30 is oriented rostrally (superiorly) and a second screw 40 is oriented caudally (inferiorly). The cage 10 can include a cavity 60 for bone product placement.

The cage 10 can also include two built in internalized screw/drill guides 80, 90 (e.g., having approximately a 25 degree angulation; in other embodiments, the angulation can be up to 40 degrees), one for each screw 30, 40, which orient the screws 30, 40 bi-directionally in opposite directions (FIGS. 2E-2G). In an embodiment, the cage includes at least one screw guide 80 or 82 having a predetermined trajectory (e.g., preferably having a 25 degree angulation) that may make placement of all screws equally facile, more amenable to multi-level placement, and may diminish the need for external drill guides. In other embodiments, the cage includes at least two screw guides 80, 82 having a predetermined trajectory (e.g., preferably having a 25 degree angulation) that may make placement of all screws equally facile, more amenable to multi-level placement, and may diminish the need for external drill guides. In other embodiments, the cage can include a screw guide 80, 82 having another predetermined trajectory, such as an angulation of substantially 25 degrees (e.g., an angulation ranging from 20 degrees to 30 degrees). In other embodiments, the cage can include a screw guide 80, 82 having another predetermined trajectory, such as an angulation ranging from 20 degrees to 25 degrees, an angulation ranging from 25 degrees to 30 degrees, an angulation ranging from 25 degrees to 35 degrees, an angulation ranging from 25 degrees to 35 degrees, an angulation ranging from 20 degrees to 40 degrees, an angulation ranging from 25 degrees to 40 degrees, etc. The embodiments of the cage can include one or more screw/drill guides 80, 82 having different angles and/or different positions within the cage.

The cage 10 can include a screw guide tunnel exit 13 adjacent to the bone cavity 60 (FIG. 2D). The screw guide tunnel can be configured to narrow along the length of the tunnel in a direction of descent into the cage 10. One of ordinary skill in the art will recognize that the internalized screw/drill guides 80, 90 can have different degrees of angulation and/or different positions within the cage 10. The built in tunnels of the screw guides 80, 90 provide an important advantage of ensuring that only a single pre-scribed angled trajectory is possible for transvertebral screw placement. The built in tunnels narrow (cone down) going downward. This facilitates the locking of the screw head to the top of the cage even in the absence of the locking mechanism described herein. Embodiments of the intervertebral cages 10 can be designed with internalized screw/drill guides 80, 90 with different angles and/or different positions within the cage. The angle and size of the screws 30, 40 make them amenable to single or multi-level placement. The superior and inferior surfaces or edges of the lumbar cage 10 can include ridges 50 or the like to facilitate integration and fusion with superior and inferior vertebral bodies. Any other method of bone integration may be used, such as, e.g., spikes in varying sizes and geometric arrays.

The embodiment can include a vertical hemi-bracket 20 which can be, for example, snapped into the superior and inferior upper wall indentations 70 in between the two screws guides 80, 90 located on top of the cage 10. The vertical hemi-bracket 20 can be manufactured from a variety of materials, such as titanium. When the screws 30, 40 are turned, the first screw member 30 and the second screw member 40 are locked in a final position by its final turn when the screw head is flush with the surface of the cage 10. The narrowing (coning down) of the internal screw guides 80, 90 acts as an initial preliminary screw locking mechanism by hugging the top of the screw at its junction with the screw head. The vertical hemi-bracket 20 which covers the medial aspect or head of both screws 30, 40 (or a portion thereof), and when snapped into the cage indentations 70 prevents screw back out or pull out from the tunnels of the cage. These novel exemplary embodiments are quite unique and different from all other conventional screw locking mechanisms.

Figure 3A:
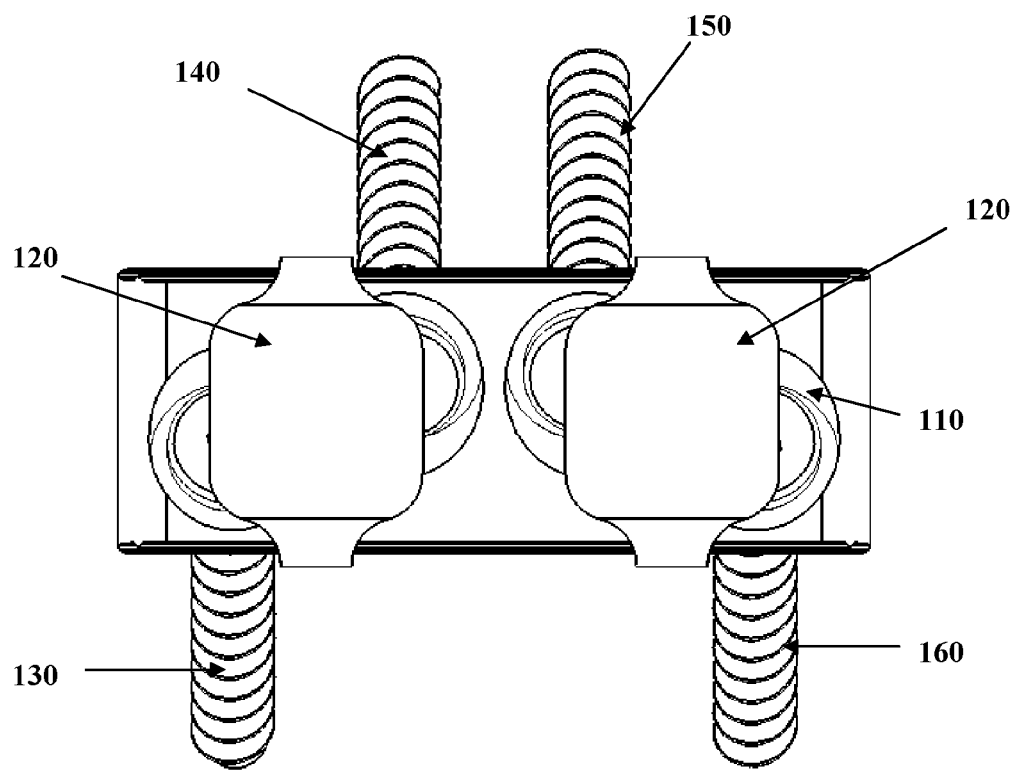
FIG. 3A illustrates a top view of an anterior lumbar intervertebral cage/BDFT screw construct according to an embodiment of the invention.
Figure 3B:
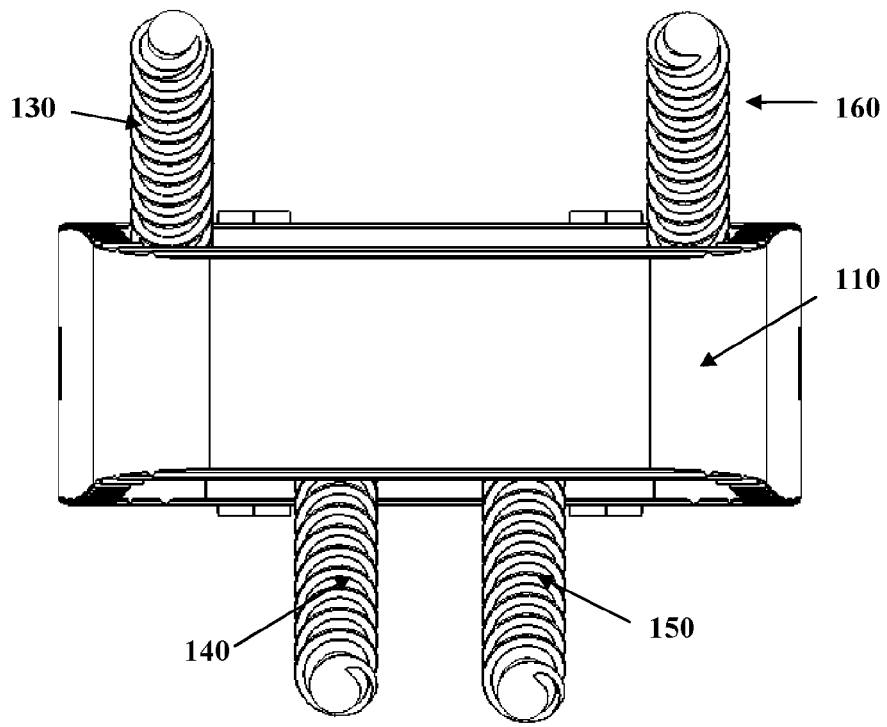
FIG. 3B illustrates a bottom view of an anterior lumbar intervertebral cage/BDFT screw construct according to an embodiment of the invention.
Figure 3C:
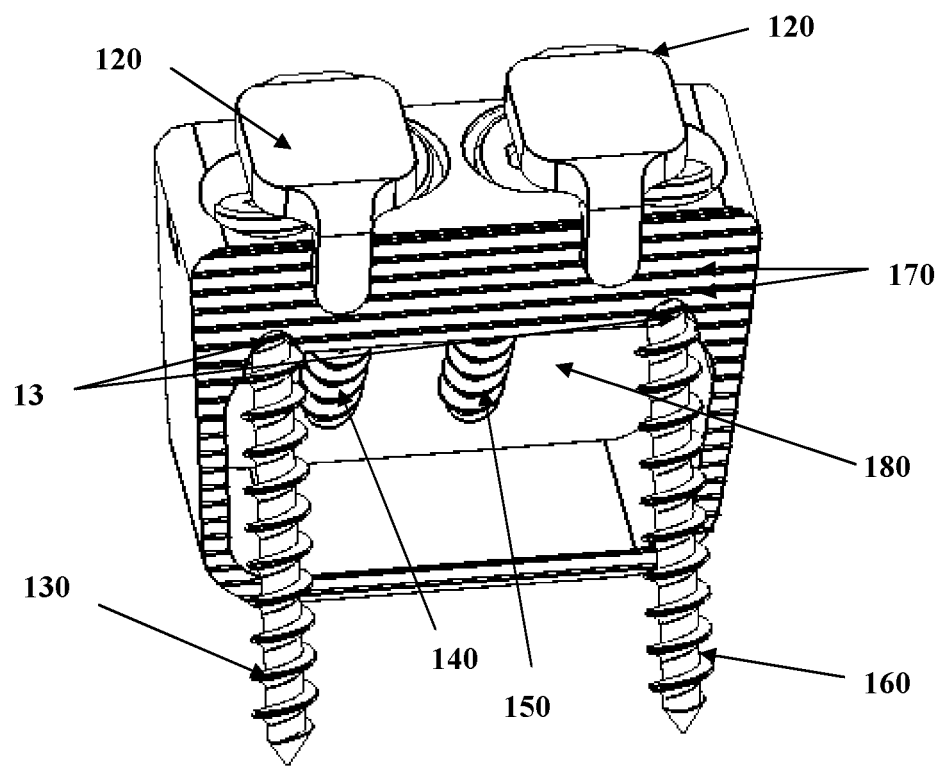
FIG. 3C illustrates a front, perspective view of an anterior lumbar intervertebral cage/BDFT screw construct according to an embodiment of the invention.
Figure 3D:
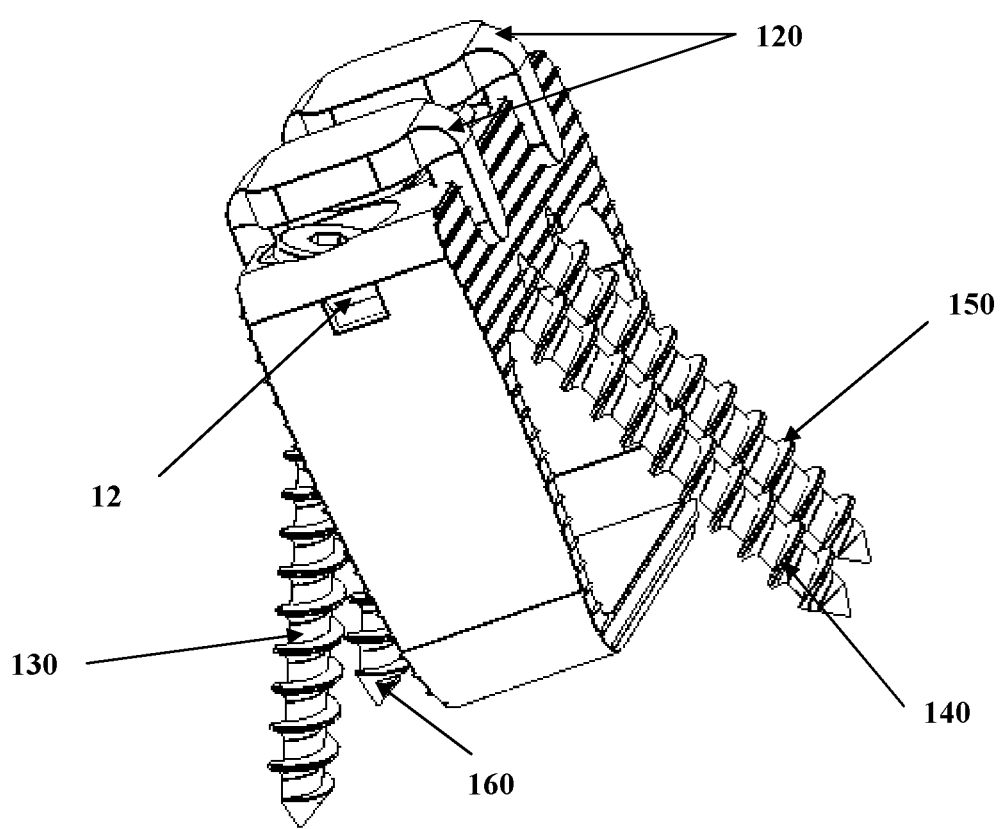
FIG. 3D illustrates a side, perspective view of an anterior lumbar intervertebral cage/BDFT screw construct according to an embodiment of the invention.
Figure 3E:
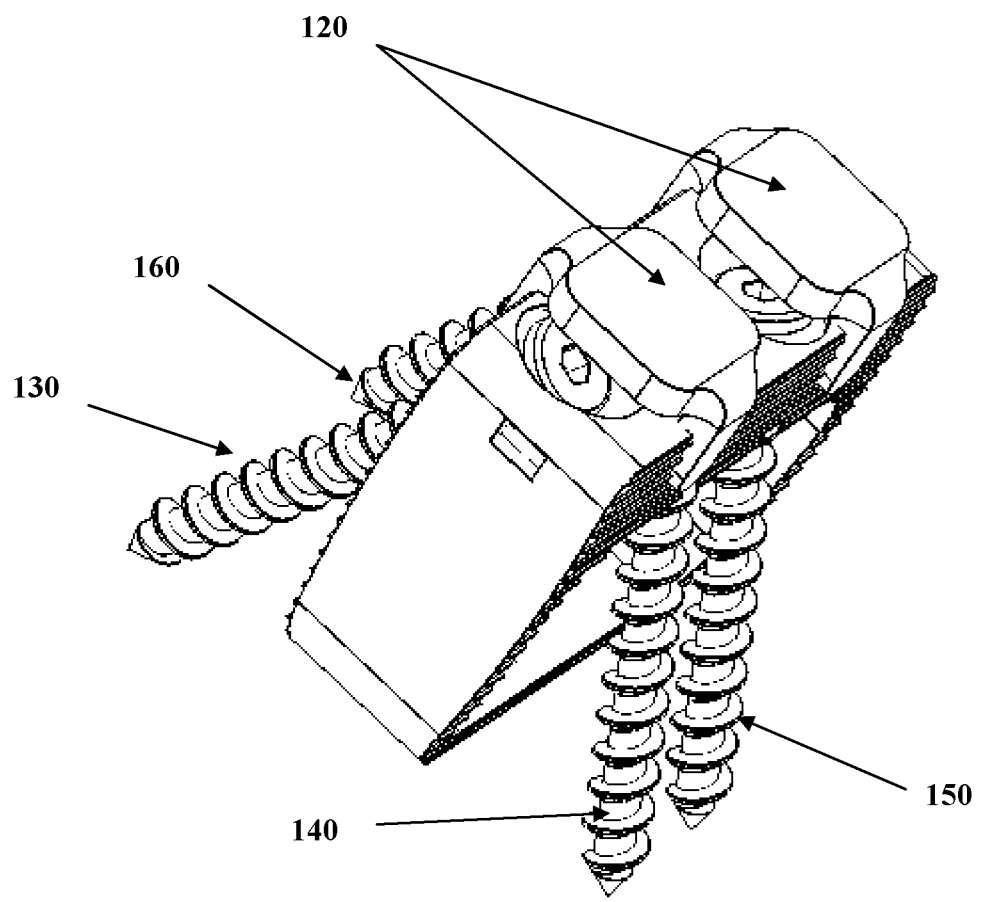
FIG. 3E illustrates a side, perspective view of an anterior lumbar intervertebral cage/BDFT screw construct according to an embodiment of the invention.
Figure 3F:
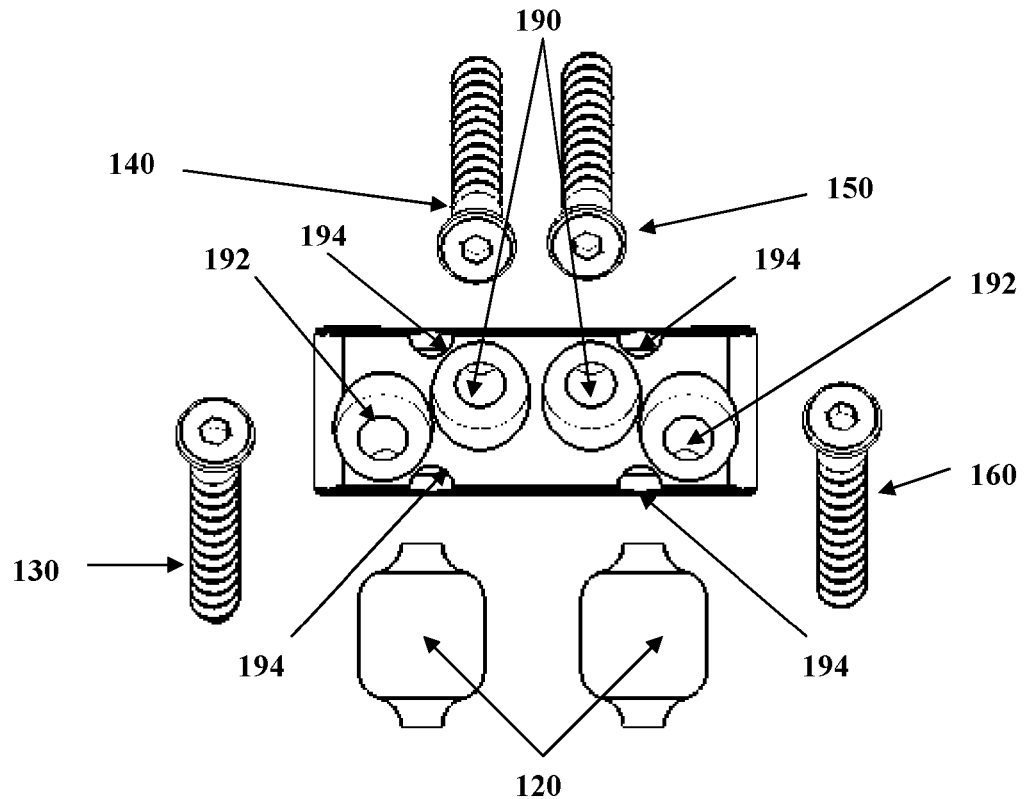
FIG. 3F illustrates a top, partially exploded view of an anterior lumbar intervertebral cage/BDFT screw construct according to an embodiment of the invention.
Figure 3G:
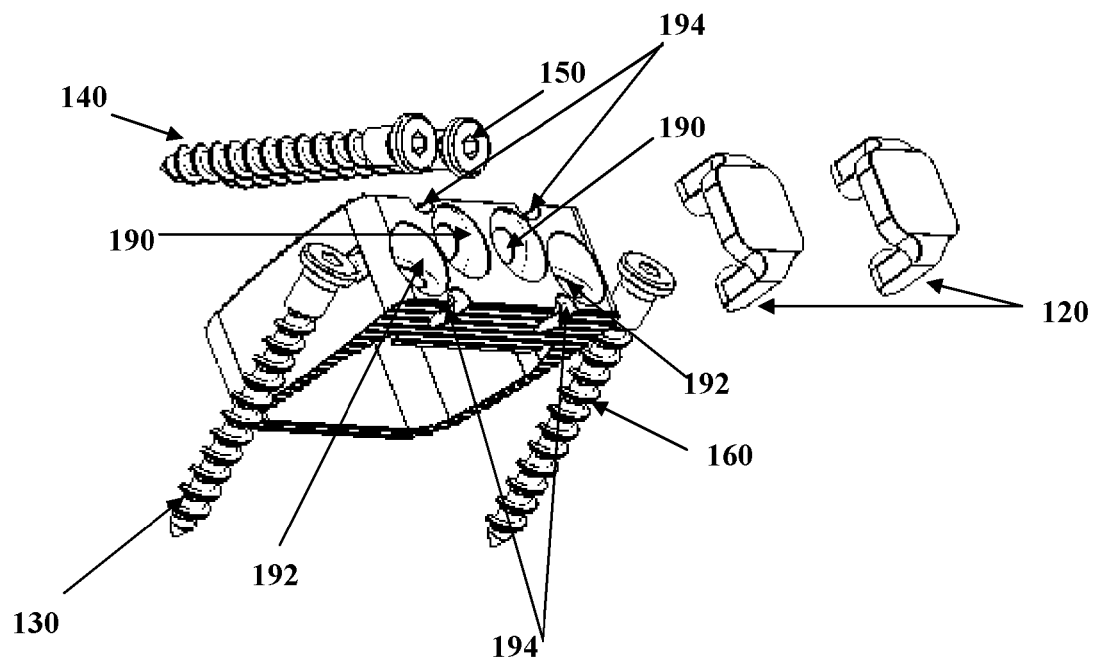
FIG. 3G illustrates a perspective, exploded view of an anterior lumbar intervertebral cage/BDFT screw construct according to an embodiment of the invention.

FIGS. 3A-3G illustrate three-dimensional views of an exemplary embodiment of an anterior lumbar intervertebral cage/BDFT construct. In this embodiment, the cage 110 includes indentations 194 on the upper superior and inferior walls of the top portion of the cage 110 midway between each of the two adjacent internalized screw guides 190, 192 (FIGS. 3F-3G). The two vertical hemi brackets 120 can snap into each of the indentations 194 such that there is one bracket 120, for each pair of adjacent screws (i.e. one for screws 130, 140, and one for screws 150, 160). In the embodiment, the screws 130, 140 and screws 150, 160 are locked into the tunnels of the cage 110 with the two hemi-brackets 120. The cage 110 can include additional indentations 12 on both side surfaces for insertion of prongs of an implantation tool. Further, cage 110 can be larger than the cervical cage 10 and also can include an elliptically contoured sidewalls when viewed from the side to fit into the bi-concave lumbar disc space (FIG. 3D). The cage 110 may include four (4) horizontally aligned internalized screw guides 190, 192 for four (4) screws 130, 140, 150, 160. The two lateral (left and right) screws 130, 160 can be oriented inferiorly, and the two middle screws 140, 150 can be oriented superiorly. The axes of these guides 190, 192 and screws 130, 140, 150, 160 are not perfectly horizontal with respect to each other. Each lateral screw guide/screw can be obliquely oriented with respect to its adjacent medial screw guide/screw. In this manner, the exemplary embodiments can achieve the proper trajectory for bone penetration along with the precise angle of the screw guides 190, 192. The screw guide tunnel exits 13 are illustrated in FIG. 3C and are in continuity (connected) with the enlarged bone cavity 180. In the embodiment, the orientations of the four screw guides 190, 192 (and screws 130, 140, 150, 160) are selected because of their symmetry and inherent stability.

The cage 110 can include a large cavity 180 for bone product placement. The cage 110 can include four built-in internalized screw/drill guides 190, 192 (e.g., having an approximate 25 degree angulation; in other embodiments, the angulation can be up to 40 degrees), one for each screw 130, 140, 150, 160. Other embodiments of the intervertebral cage 110 can be designed with internalized screw/drill guides 190, 192 with different angles and/or different positions within the cage 110. The angle and size of the screws 130, 140, 150, 160 make them amenable to single or multi-level placement. The superior and inferior surfaces or edges of the cage 110 can include ridges 170 or the like to facilitate integration and fusion with superior and inferior vertebral bodies. Other bone integration embodiments such as spikes can also be used. In this embodiment, there are no compartmental divisions in the cavity 180 for bone product placement to maximize the quantity of bone for fusion.

In this embodiment, there is one vertical hemi bracket 120 for two screws 130, 140, 150, 160. Yet, in other embodiments, one vertical hemi bracket 120 can be provided for each individual screw 130, 140, 150, 160, or vertical hemi bracket 120 can be provided for two or more screws 130, 140, 150, 160. The top of the cage 110 can include indentations 194 on the superior and inferior upper sides of the cage 110 that are engaged the vertical hemi bracket 120 (e.g., by snapping a portion of the bracket into the indentation 194). The bracket 120 can be manufactured from a variety of materials, such as bio-compatible materials, such as titanium.

In operation, when each of the screws 130, 140, 150, 160 are turned, each of the screws 130, 140, 150, 160 is locked in a final position by a final turn of the screw when the screw head is flush with the surface of the cage 110. The narrowing of the internal screw guides 190, 192 can act as an initial preliminary screw locking mechanism by hugging the top of the screw/screw head interface (e.g., at its junction with the screw head). One vertical hemi-bracket 120 covers the medial aspect (or portion thereof) of the first two screws, 130, 140, and another vertical hemi bracket 120 covers the medial aspect (or portion thereof) of the third and fourth screws 150, 160. When the brackets are snapped and/or locked into the cage indentations 194, screw back out or pull out of all fours screws can be prevented.

The internal screw guide tunnels 190, 192 can be formed to narrow along a length of the screw guide in a direction of descent into the screw guides, thereby providing a preliminary first locking mechanism when the screws 130, 140, 150, 160 engage the screw guides and are countersunk into the top of the cage 110. The exemplary embodiments of the bracket 120, which are locked into the cage 110 and cover at least a portion of the screw heads, can provide a secondary additive locking mechanism in combination with the first locking mechanism, thereby definitively preventing screw back out. In other embodiments, only the exemplary embodiments of the bracket 120, which is locked into the cage 110 and covers the screw heads (or a part of the screw heads), may be provided to function as a primary locking mechanism for definitively preventing screw back out.

The exemplary embodiments are an evolutionary advance and improvement to the apparatus illustrated in the aforementioned related applications of Applicants, and are quite unique and different from all other conventional locking mechanisms used for other types of anterior lumbar cages.

For example, a known conventional device has been provided that relates to anterior placed lumbar implants with perforating screws. Such possible conventional devices conceivably may include a horseshoe implant having a plurality of cylindrical holes with smooth inner surfaces and comprise only one stop for the heads of the bone screws to be inserted into them. The placement of five cylindrical holes is oriented within the cage in a non-symmetric manner.

In comparison, the exemplary embodiments differ in many substantial ways from the conventional devices. For example, the exemplary embodiments provide a symmetric orientation of the screw holes, as well as a screw locking mechanism. The exemplary embodiments also provide an angulation/trajectory (e.g., an approximate twenty five degree angulation/trajectory) for preventing pull-out or back-out of the screws that would make placement of all screws in a manner which would lead to maximum stability of the construct within the vertebral space, and obviate the need for external drill guides, and surgeon trajectory angulation guess work.

In another possible conventional device, multiple embodiments of lumbar intervertebral implants are presented which include one with internally threaded bore holes, another embodiment with a front plate mounted at the front surface of the implant, and another embodiment with the front place displaceably configured to move vertically relative to the implant. In addition, such devices may provide preferred borehole axes of 35-55 degrees. These conventional devices may have four screw perforations that are not aligned four in a row. Two of the screw holes are laterally placed on the left, one on top of each other, the top one with a superior trajectory, and the bottom with an inferior trajectory. Likewise, two perforations are placed on the right, one on top of each other, the top one with a superior trajectory and the bottom one with an inferior trajectory. The disclosed screw locking mechanism is a screw with an external thread matching the internal borehole thread, or spiral springs.

In comparison, the anterior lumbar construct of the exemplary embodiments differs in many substantial ways from the conventional devices. The exemplary embodiments include a single cage construct with four (4) internalized drill guides arranged horizontally in a row. The lateral screw guides/screws are obliquely oriented with the respect to their adjacent medial screw guides/screws. The middle two screws are oriented superiorly, and the lateral left and right screws are oriented inferiorly. This symmetric alignment of screws and orientations within the superior and inferior vertebral bodies (e.g., two middle superiorly projecting screws, and two laterally projecting inferior screws) make the fixation to the superior and inferior vertebral bodies much more symmetric and thus more stable, thereby preventing subsidence. In an exemplary embodiment, the cage includes a screw guide having a predetermined trajectory (e.g., an approximate trajectory of 25 degrees to 40 degrees) that makes placement of all screws equally facile, more amenable to multi-level placement, and diminishes the need for external drill guides. Furthermore, the exemplary screw locking mechanism is unique and differs substantially from the conventional approach of matching screw/cage threads or spiral springs.

Figure 4A:
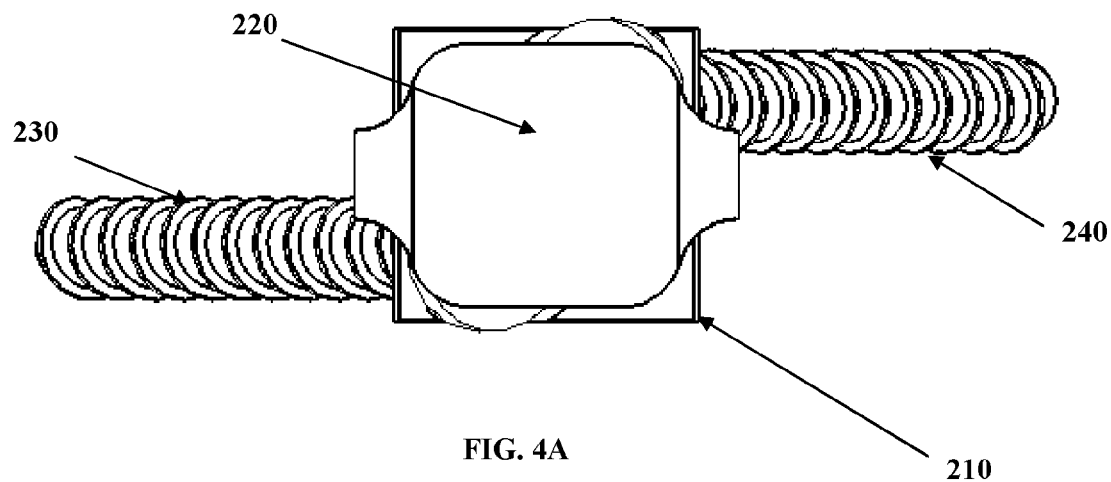
FIG. 4A illustrates a top view of a posterior lumbar rectangularly designed intervertebral cage/BDFT construct according to an embodiment of the invention.
Figure 4B:
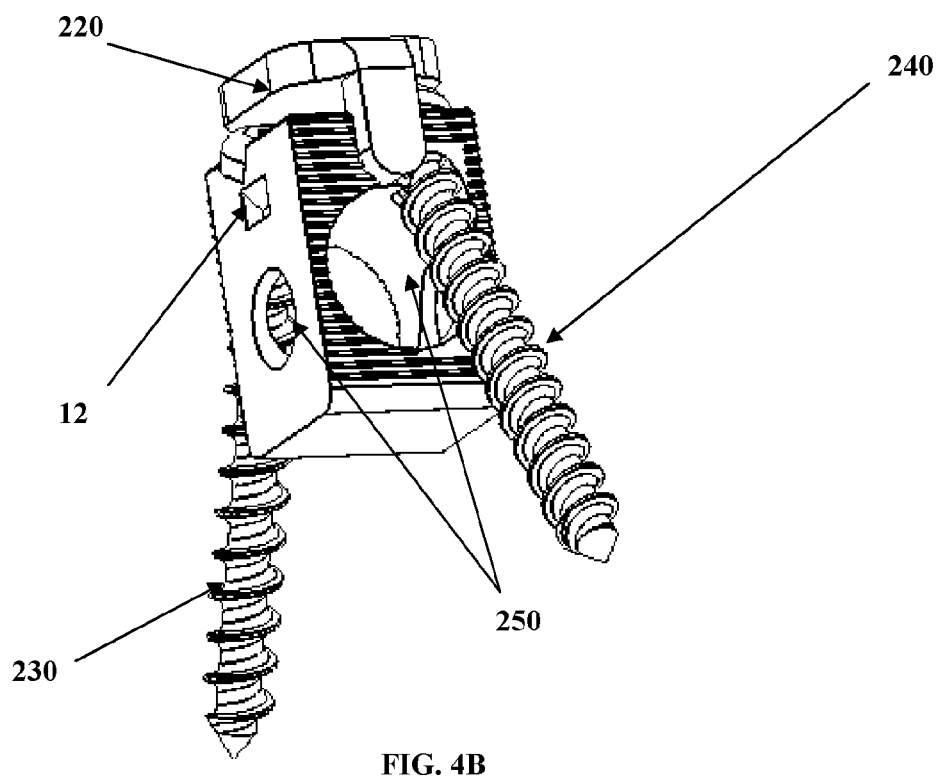
FIG. 4B illustrates a front, perspective view of a posterior lumbar rectangularly designed intervertebral cage/BDFT construct according to an embodiment of the invention.
Figure 4C:
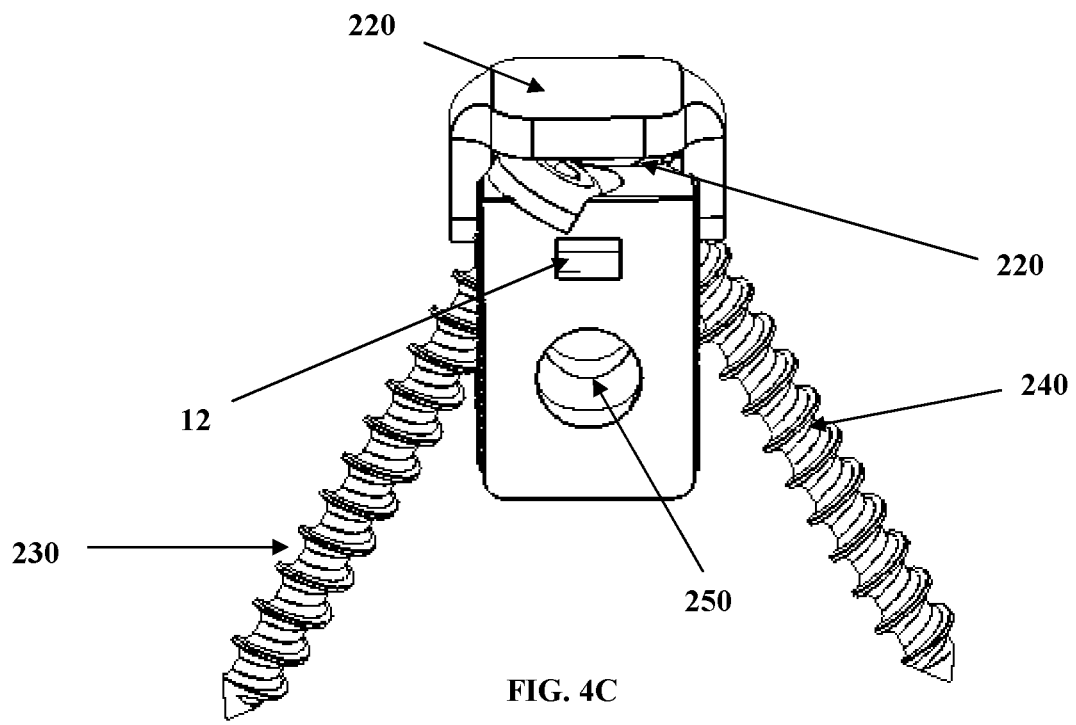
FIG. 4C illustrates a side, perspective view of a posterior lumbar rectangularly designed intervertebral cage/BDFT construct according to an embodiment of the invention.
Figure 4D:
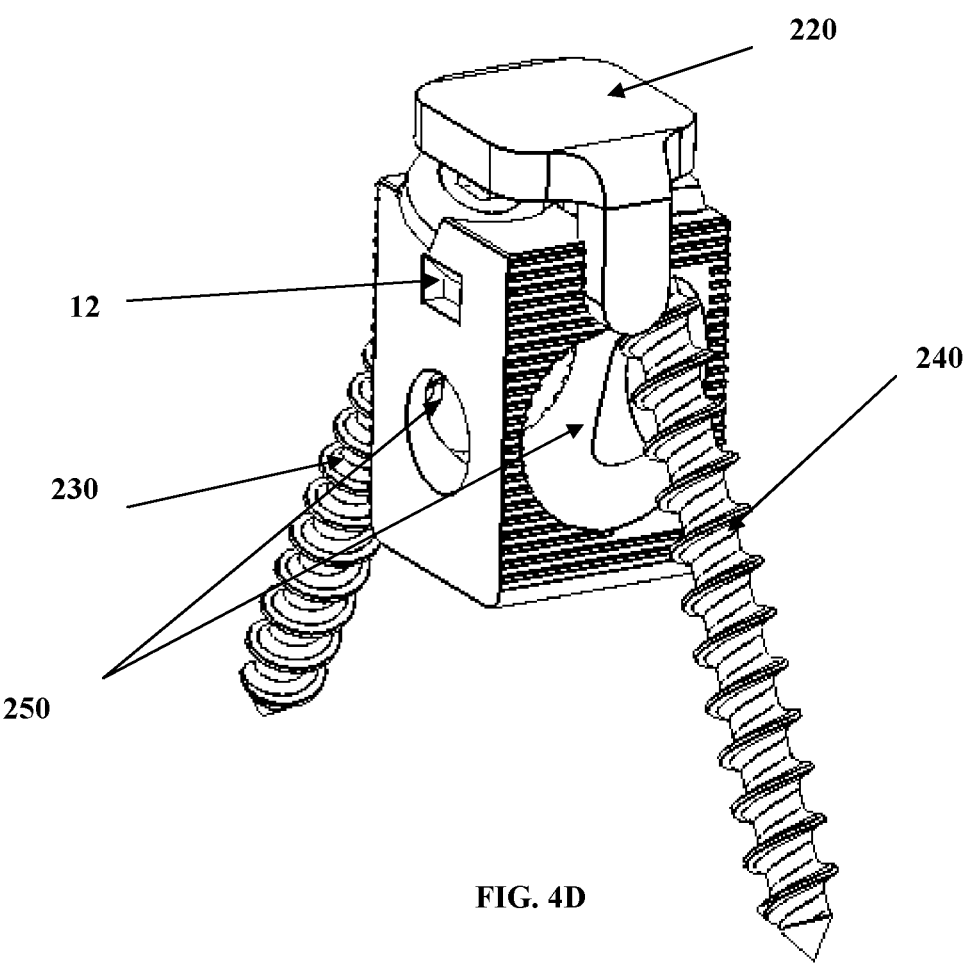
FIG. 4D illustrates a front, perspective view of a posterior lumbar rectangularly designed intervertebral cage/BDFT construct according to an embodiment of the invention.
Figure 4E:
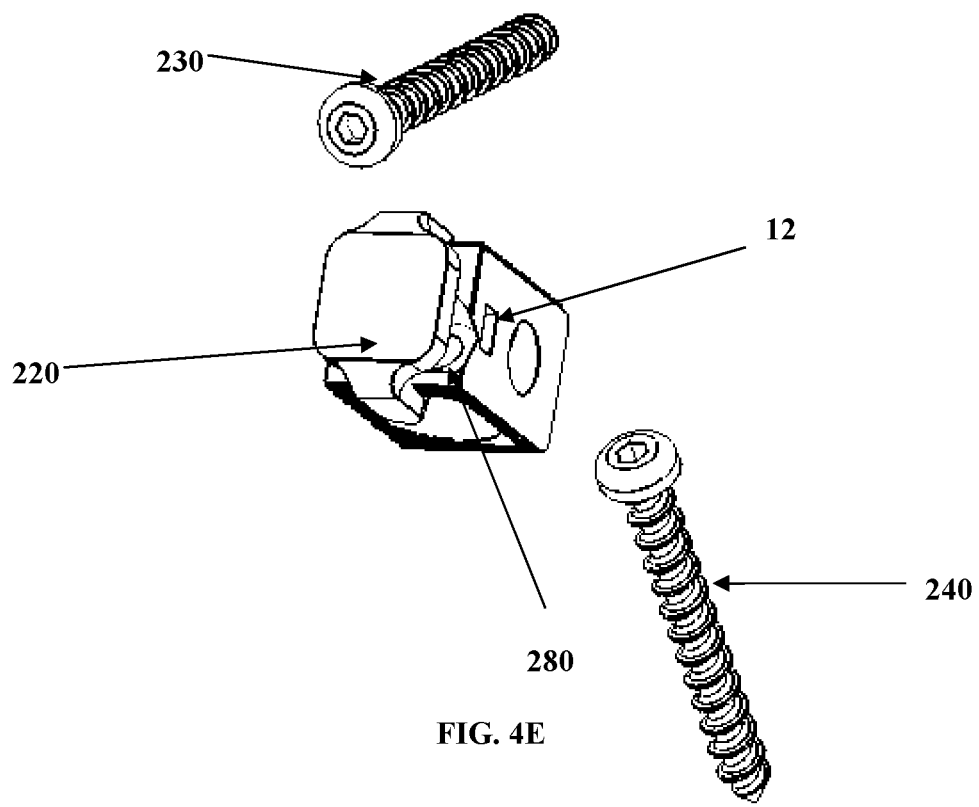
FIG. 4E illustrates a top, perspective, partially exploded view of a posterior lumbar rectangularly designed intervertebral cage/BDFT construct according to an embodiment of the invention.
Figure 4F:
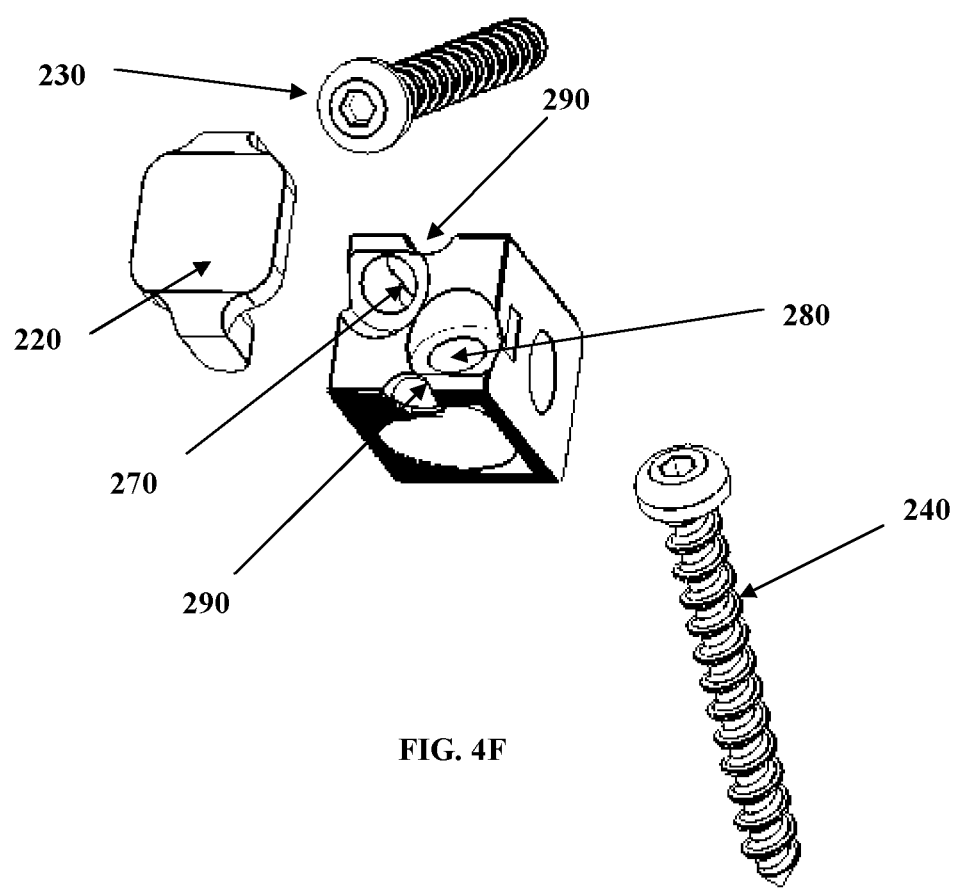
FIG. 4F illustrates a top, perspective, exploded view of a posterior lumbar rectangularly designed intervertebral cage/BDFT construct according to an embodiment of the invention.

FIGS. 4A-4F illustrate three-dimensional views of an exemplary embodiment of a posterior lumbar rectangular intervertebral cage/BDFT construct. In this embodiment, the top portion of the cage 210 includes indentations 290 that are positioned on the upper superior and inferior walls midway between the two internalized screw guides 270, 280 (FIG. 4F). The vertical hemi bracket 220 snaps into these indentations 290. The cage 210 also includes additional indentations 12 on both side surfaces of the construct for the prong placement of an implantation tool. The screws 230, 240 perforate and orient in opposing superior and inferior directions.

The cage 210 can include a cavity 250 for bone product placement. In an exemplary embodiment, a side surface of the cage 210 can be elliptically contoured when viewed from the side (FIG. 4C) to fit into the bi-concave cervical disc space. In an exemplary embodiment, the top and bottom portions of the rectangular cage 210 can be elliptically contoured to naturally fit into the bi-concave intervertebral disc space (FIG. 4C). The top portion of the cage can be square-shaped with equal width and length. Also, in contrast to the cervical cage 10 of the previous embodiments, the depth dimension of the cage 210 far exceeds its width. The width is very narrow to prevent nerve root retraction/injury when being placed posteriorly. The cage 210 can also include built-in internalized screw/drill guides 270, 280 having a predetermined angled trajectory (e.g., having an approximate 25 to 40 degree angulation), and their axes are not horizontal, but oblique one to the other and very close to each other (FIG. 4F). Each screw/drill guides 270, 280 can occupy one corner of a square, obliquely oriented one to the other (FIGS. 4A and 4F). This is necessary to achieve proper screw angulation, trajectory and bone penetration in a narrow posterior lumbar interspace. One of the screw guides is angled rostrally (superiorly) (e.g., screw guide 270) and the other caudally (inferiorly) (e.g., screw guide 280). The intervertebral cages 210 can be designed with internalized screw/drill guides 270, 280 with different angles and/or different positions within the cage 210. Because the tunnel of the screw guide 270, 280 narrows (cones down), when the screw 230, 240 is countersunk on top of the cage 210, the screw 230, 240 can be preliminarily locked, even in the absence of this locking mechanism. The cage 210 can include the narrowing tunnel and/or bracket 220 for preventing backing out of the screws. The angle and size of the screws 230, 240 make them amenable to single or multi-level placement. A screw guide exit tunnel can be formed adjacent to the bone cavity 250. The superior and inferior surfaces or edges can include ridges or the like to facilitate integration and fusion with superior and inferior vertebral bodies. The surfaces could alternatively or in supplement, have additional bone integration mechanisms, e.g. spikes having various sizes and arrangements. One of these constructs is placed posteriorly into the intervertebral space either on the left side, the right side, or both sides.

An embodiment can also include a cage 210 which includes a vertical hemi bracket locking mechanism 220 that can be, for example, snapped into the indentations 290 on the upper aspects of the superior and inferior sides of the cage 210. The vertical hemi bracket locking mechanism 220 can be manufactured from a variety of materials, such as bio-compatible materials, such as titanium. In operation, when the screws 230, 240 are turned, each of the first screw member 230 and the second screw member 240 is locked in a final position by a final turn of the screw when the screw head is flush with the surface of the cage 210. The narrowing of the internal screw guides 270, 280 can act as an initial preliminary screw locking mechanism. The vertical hemi-bracket 220 covering the medial aspect (or a portion thereof) of both screws 230, 240 when snapped into the cage indentations 290 can prevent screw back out or pull out.

These novel exemplary embodiments are quite unique and different from all other conventional screw locking mechanisms.

Figure 5A:
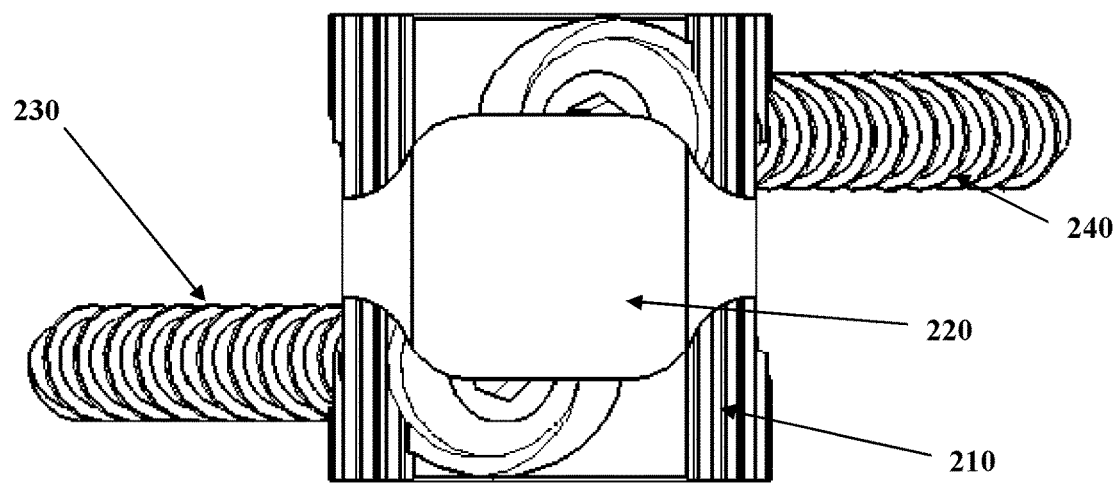
FIG. 5A illustrates a top view of a posterior lumbar elliptically designed intervertebral cage/BDFT construct according to an embodiment of the invention.
Figure 5B:
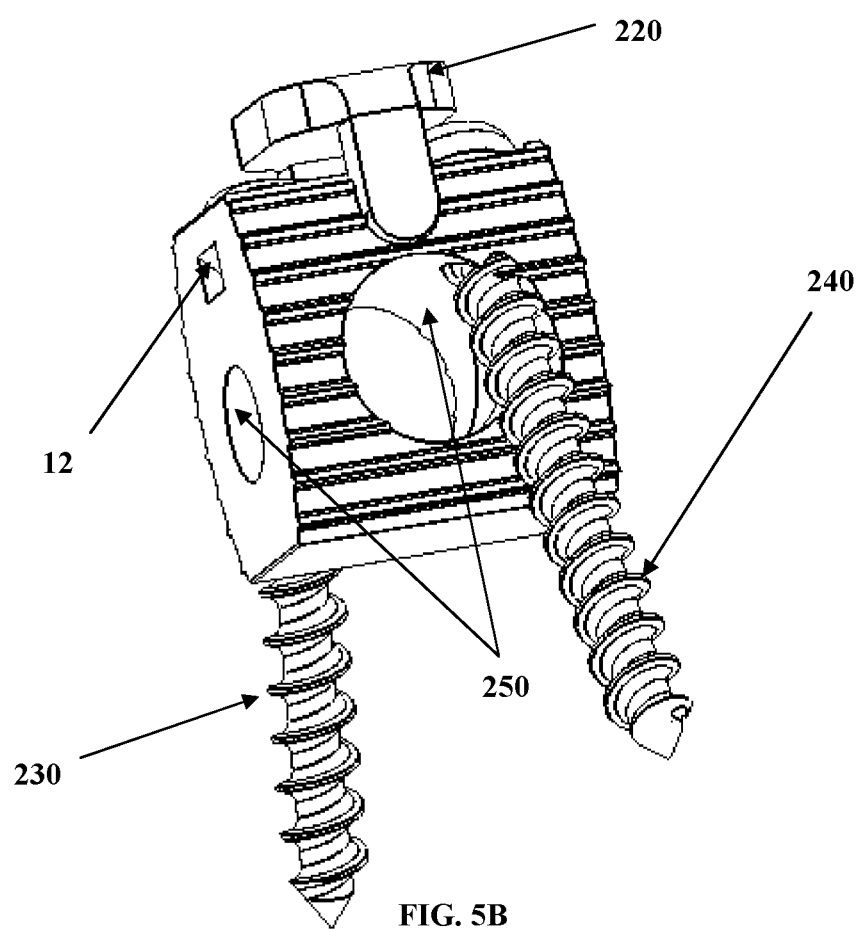
FIG. 5B illustrates a front, perspective view of a posterior lumbar elliptically designed intervertebral cage/BDFT construct according to an embodiment of the invention.
Figure 5C:
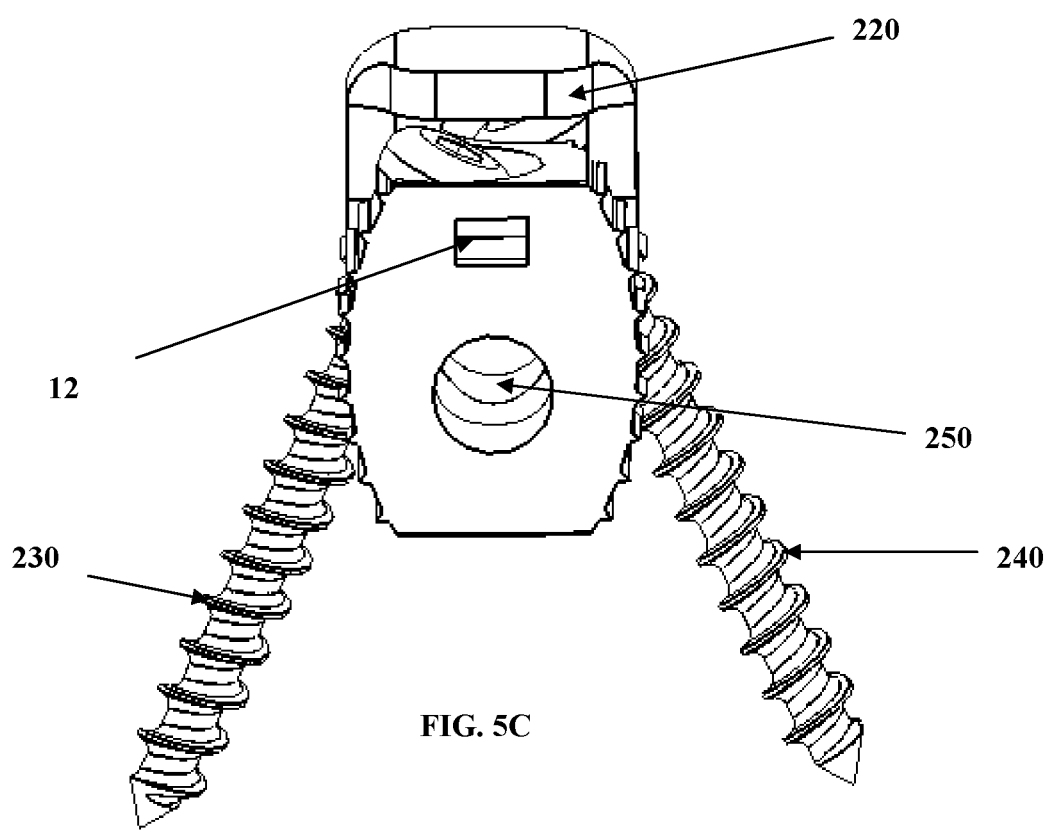
FIG. 5C illustrates a side view of a posterior lumbar elliptically designed intervertebral cage/BDFT construct according to an embodiment of the invention.
Figure 5D:
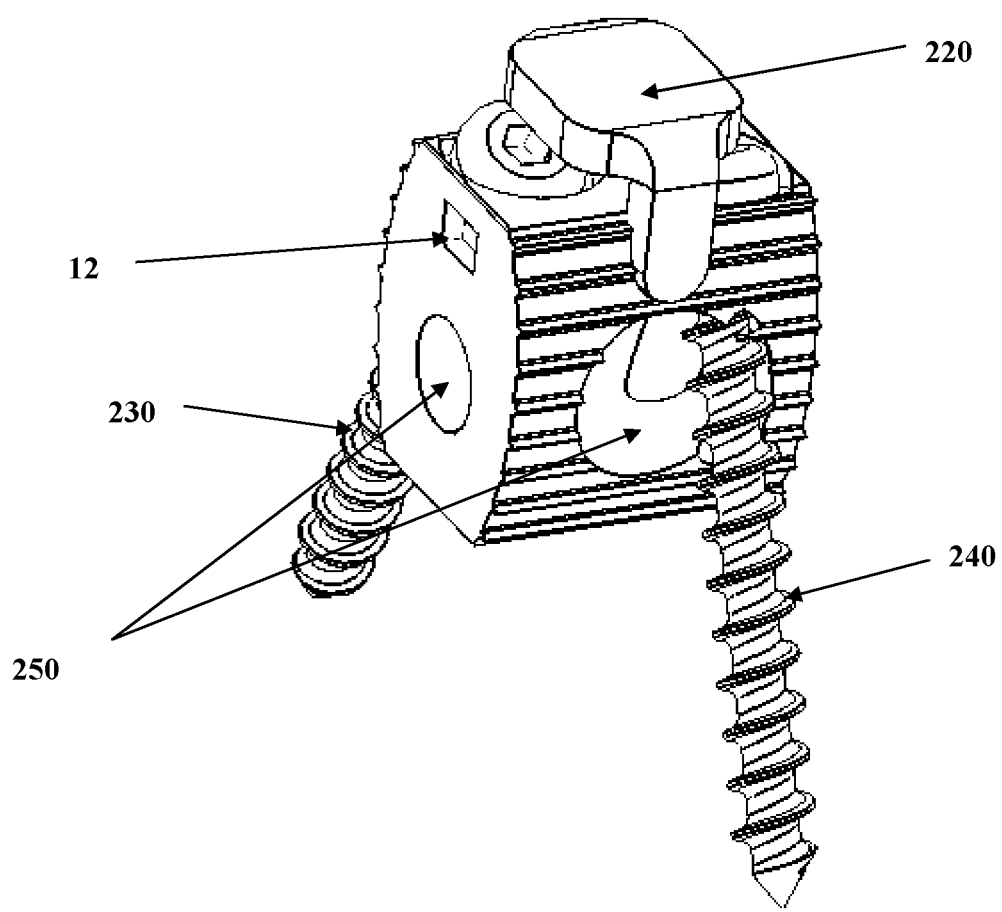
FIG. 5D illustrates a front, perspective (front isometric) view of a posterior lumbar elliptically designed intervertebral cage/BDFT construct according to an embodiment of the invention.
Figure 5E:
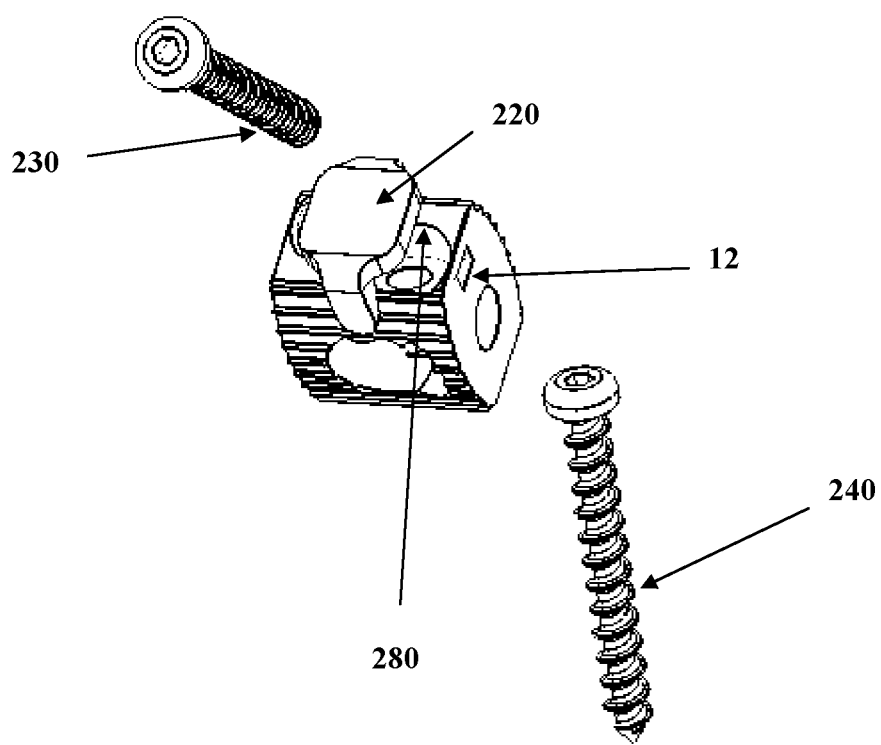
FIG. 5E illustrates a top, perspective, partially exploded view of a posterior lumbar elliptically designed intervertebral cage/BDFT construct according to an embodiment of the invention.
Figure 5F:
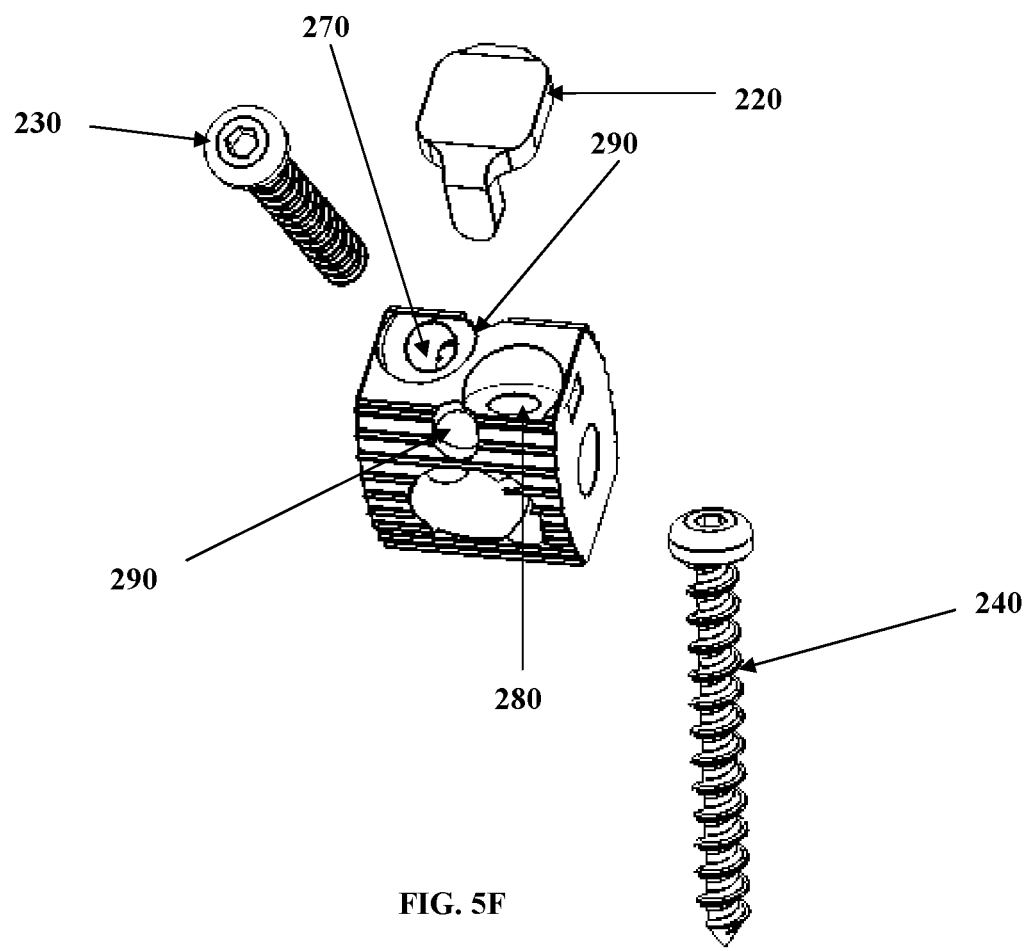
FIG. 5F illustrates a top, perspective, exploded view of a posterior lumbar elliptically designed intervertebral cage/BDFT construct according to an embodiment of the invention.

FIGS. 5A-5F illustrates three-dimensional views of an exemplary embodiment of a posterior lumbar elliptical intervertebral cage/BDFT construct. In this embodiment, the top portion of the cage 210 includes indentations 290 that are positioned on the upper superior and inferior walls midway between the two internalized screw guides/screws 270, 280 (FIG. 5F). The vertical hemi bracket 220 snaps into these indentations 290. The cage 210 also includes additional indentations 12 on both side surfaces of the construct for the prong placement of an implantation tool. The screws 230, 240 perforate and orient in opposing superior and inferior directions.

The cage 210 can include a cavity 250 for bone product placement. In an exemplary embodiment, the entire body (or at least the side walls) of the cage 210 is elliptical when viewed from the side (FIG. 5C), as opposed to the top and bottom portions of the rectangular cage 210 described in the previous embodiment (FIG. 4C). Further, in this embodiment, the cage 210 can be contoured to naturally fit into the bi-concave intervertebral disc space (FIG. 5C).

The cage 210 can also include built-in internalized screw/drill guides 270, 280 having a predetermined angled trajectory (e.g., having an approximate 25-40 degree angulation), and their axes are not horizontal or vertical, but oblique one to the other and very close to each other. Each screw guide/screw occupies one corner of a square, obliquely oriented one to the other (FIGS. 5A and 5F). In this manner, the exemplary embodiment can achieve proper screw angulation, trajectory, and bone penetration in so narrow a posterior lumbar interspace. One of the screw guides can be angled rostrally (superiorly) (e.g., screw guide 270) and the other caudally (inferiorly) (e.g., screw guide 280). The intervertebral cages 210 can be designed with internalized screw/drill guides 270, 280 with different angles and/or different positions within the cage 210. In an embodiment, the tunnel of the screw guide 270, 280 narrows (cones down) and hugs the screw(s) 230, 240 at the screw-screw head interface such that, when the screw is countersunk on top of the cage 210, the screw(s) 230, 240 can be preliminarily locked, even in the absence of an additional locking mechanism. The exemplary embodiments of the bracket 220, which are locked into the cage 210 and cover at least a portion of the screw heads, can provide a secondary additive locking mechanism in combination with the first locking mechanism provided by the screw guides, thereby definitively preventing screw back out. In other embodiments, only the exemplary embodiments of the bracket 220, which is locked into the cage 210 and covers the screw heads (or a part of the screw heads), may be provided to function as a primary locking mechanism for definitively preventing screw back out. The angle and size of the screws 230, 240 make them amenable to single or multi-level placement. The screw guide exit tunnel 13 adjacent to the bone cavity 250 is illustrated in FIG. 5B. The superior and inferior surfaces or edges can include ridges or the like to facilitate integration and fusion with superior and inferior vertebral bodies. One of these constructs is placed posteriorly into the intervertebral space either on the left side, the right side, or both sides.

The embodiment can include a cage 210 which includes a vertical hemi bracket locking mechanism 220 that can be, for example, snapped into the indentations 290 on the upper aspects of the superior and inferior sides of the cage 210. The vertical hemi bracket locking mechanism 220 can be manufactured from a variety of materials, such as titanium. When the screws 230, 240 are turned, the first screw member 230 and the second screw member 240 are locked in a final position by its final turn when the screw head is flush with the surface of the cage 210. The narrowing of the internal screw guides 270, 280 act as an initial preliminary screw locking mechanism. The vertical hemi-bracket 220 covering the medial aspect (or a portion thereof) of both screws 230, 240 when snapped into the cage indentations 290 prevent screw back out or pull out.

The exemplary embodiment of this novel intervertebral cage 210 is an evolutionary compliment to the apparatus illustrated in the aforementioned related applications. The novel cage 210 also is quite unique and different from other conventional locking mechanisms used for other known cervical and lumbar anterior or posterior plate screws. No other conventional posterior lumbar intervertebral cage BDFT/screw constructs are known.

The embodiments have been described with reference to the exemplary embodiments illustrated in the Figures. One of ordinary skill in the art will recognize that the embodiments are not limited to the illustrated embodiments and any of the features of any of the embodiments can be included in any other embodiment.

2. Exemplary Surgical Method

Exemplary surgical steps for practicing one or more of the forgoing embodiments will now be described.

Anterior cervical spine placement of the intervertebral cage/BDFT screw construct 10 (FIG. 2) can be implanted via previously described techniques for anterior cervical discectomy and fusion. Some but not all of these techniques include, open, microscopic, closed endoscopic or tubular. Fluoroscopic or any other form of visualized guidance can be used for this procedure.

After the adequate induction of anesthesia, the patient is placed in a supine position. An incision is made overlying the intended disc space or spaces, and the anterior spine is exposed. A discectomy is performed and the endplates exposed. The disc height is measured and an anterior cervical intervertebral cage of the appropriate disc height, width and depth is selected. The central cavity 60 is packed with bone fusion material, autologous bone graft, allograft, alone or in combination with any commercially available bone fusion promoting product. The cage 10 is then inserted into the midline of the anterior disc space routinely until it is flush or countersunk relative to the vertebral body above and below. The BDFT screws 30, 40 are then inserted into the internalized rostrally (superiorly) and caudally (inferiorly) angled screw guides 80, 90. A drill with or without a drill guide can be used to prepare for screw placement. This is not absolutely necessary. Because the cage 10 has internalized screw guides 80, 90, self-drilling/self-tapping screws 30, 40 of the appropriately selected lengths can be directly screwed into the vertebral bodies once placed into the internalized drill-guided angled tunnels. The cage's screw guides 80, 90, which have internalized tunnels, direct the screws 30, 40 into the superior and inferior vertebral bodies in the predetermined angle of the internalized tunnels. There is no other angled trajectory other than that which is built into the internalized screw guide/tunnel of the cage 10 that the screw 30, 40 can be oriented in. Hence, according to this exemplary embodiment, there is no absolute need for fluoroscopic guidance.

Once the surgeon is satisfied with the position and placement of the cage 10, the BDFT screws 30, 40 can then be locked into their final positions. When each of the BDFT screws 30, 40 are turned they penetrate and engage the bone until they are locked in a final position by its final turn when the screw head is flush with the surface of the cage 10. The vertical hemi bracket 20 is then snapped into the upper superior and inferior cage indentations 70 covering the medial aspect of both screws.

Anterior or anteriolateral placement of thoracic or lumbar spine intervertebral cage/BDFT screw constructs 110 (FIG. 3) can be implanted via previously described surgical techniques for anterior lumbar discectomy, and transthoracic, anterior-lateral thoracic discectomy. Some but not all of these techniques include, open, microscopic, closed endoscopic or tubular. Fluoroscopic or any other form of visualized guidance can be used for this procedure.

After the adequate induction of anesthesia and after the anterior spine is exposed a discectomy is performed and the endplates exposed. The disc height is measured and an anterior lumbar (or thoracic) intervertebral cage 110 of the appropriate disc height, width and depth is selected. The central cavity 180 is packed with bone fusion material, autologous bone graft, allograft, alone or in combination with any commercially available bone fusion promoting product. The cage 110 is then inserted into the midline of the anterior disc space routinely until it is flush or countersunk relative to the vertebral body above and below. The four BDFT screws 130, 140, 150, 160 are then inserted into the two middle internalized rostrally (superiorly) and two lateral, caudally (inferiorly) angled screw guides 190, 192. A drill with or without a drill guide 190, 192 can be used to prepare for screw placement. This is not absolutely necessary. Because the cage 110 has internalized screw guides 190, 192, self-drilling/self-tapping screws 130, 140, 150, 160 of the appropriately selected lengths can be directly screwed into the vertebral bodies once placed into the internalized drill-guided angled tunnels. The cage's internalized guides 190, 192, which have internalized tunnels, direct the screws 130, 140, 150, 160 into the superior and inferior vertebral bodies in the predetermined angle of the internalized tunnels. There is no other angled trajectory other than that which is built into the internalized screw guide/tunnel of the cage 110 that the screw 130, 140, 150, 160 can be oriented in. Hence there is no absolute need for fluoroscopic guidance.

Once the surgeon is satisfied with the position and placement of the cage 110, the BDFT screws 130, 140, 150, 160 can then be locked into their final positions. When each of the BDFT screws 130, 140, 150, 160 are turned, they penetrate and engage the bone until they are locked in a final position by its final turn when the screw head is flush with the surface of the cage 110. One vertical hemi bracket 120 is snapped into its corresponding cage indentations 194 thereby covering the medial aspects of the first two screws 130, 140, and another vertical hemi bracket 120 is snapped into its respective cage indentations 194 thereby covering the medial aspects of the third and fourth screws 150, 160.

Implantation of the posterior lumbar intervertebral cage/BDFT screw constructs 210 (FIGS. 4 and 5) can be performed via previously described posterior lumbar interbody fusion (PLIF) or posterior transforaminal lumbar interbody fusion (TLIF) procedures. The procedures can be performed open, microscopic, closed tubular or endoscopic techniques. Fluoroscopic guidance can be used with any of these procedures.

After the adequate induction of anesthesia, the patient is placed in the prone position. A midline incision is made for a PLIF procedure, and one or two parallel paramedian incisions or a midline incision is made for the TLIF procedure. For the PLIF procedure, a unilateral or bilateral facet sparing hemi-laminotomy is created to introduce the posterior lumbar construct into the disc space after a discectomy is performed and the space adequately prepared.

For the TLIF procedure, after unilateral or bilateral dissection and drilling of the inferior articulating surface and the medial superior articulating facet the far lateral disc space is entered and a circumferential discectomy is performed. The disc space is prepared and the endplates exposed.

The disc height is measured and a posterior lumbar intervertebral cage/BDFT screw construct 210 (FIGS. 4 and 5) of the appropriate disc height, width and depth is selected. The central cavity 250 is packed with bone fusion material, autologous bone graft, allograft, alone or in combination with any commercially available bone fusion promoting product. Then one construct 210 is placed on either right or left sides, or one construct 210 each is placed into left and right sides. The constructs 210 are inserted such they are flush or countersunk relative to the superior and inferior vertebral bodies. In addition to the central cavities 250 that are packed with bone product, the intervertebral space in between the constructs 210 can also be packed with bone product for fusion.

The BDFT screws 230, 240 are then inserted into internalized rostrally (superiorly) and caudally (inferiorly) angled screw guides 270, 280. A drill with or without a drill guide can be used to prepare for screw placement. This is not absolutely necessary. Because the cage 210 has internalized screw guides 270, 280, self-drilling/self-tapping screws 230, 240 of the appropriately selected lengths can be directly screwed into the vertebral bodies once placed into the internalized drill-guided/angled tunnels 270, 280. The cage's internalized guides 270, 280, which have internalized tunnels, direct the screws 230, 240 into the superior and inferior vertebral bodies in the predetermined angle of the internalized tunnels. There is no other angled trajectory other than that which is built into the internalized screw guide/tunnel 270, 280 of the cage 210 that the screw 230, 240 can be oriented in. Hence, unlike posterior placement of pedicle screws there is no absolute need for fluoroscopic or expensive and cumbersome, frameless stereotactic CT guidance.

Once the surgeon is satisfied with the position and placement of the cage 210, the BDFT screws 230, 240 can then be locked into their final positions. When each of the BDFT screws 230, 240 with ratcheted screw heads are turned, the BDFT screws 230, 240 penetrate and engage the bone until they are locked in a final position by its final turn when the screw head is flush with the surface of the cage 210. The vertical hemi bracket 220 is then snapped into the upper superior and inferior cage indentations 290 of the cage 210 covering the medial aspect of both screws 230, 240 and thus preventing screw back out or pull out.

The present inventions may provide effective and safe techniques that overcome the problems associated with current transpedicular based cervical, thoracic and lumbar fusion technology, as well as anterior cervical, thoracic and lumbar plating technology, and for many degenerative stable and unstable spinal diseases. These exemplary embodiments may replace much pedicle screw, and anterior plating based instrumentation in many but not all degenerative spine conditions.

The speed and simplicity of placement of anterior and posterior lumbar intervertebral cage/BDFT screw constructs, and placement of anterior cervical cage/BDFT screw constructs far exceeds that of current pedicle screw and anterior spinal plating technology. Furthermore, these devices have markedly significantly decreased risk of misguided screw placement and hence decreased risk of neurovascular injury, and blood loss. The lumbar and cervical intervertebral cage/BDFT screw constructs all would have decreased recovery time, and more rapid return to work time compared to pedicle screw, and plating technology. These devices with great probability lead to similar if not equal fusion rates, with substantially less morbidity, and hence, overall, make them a major advance in the evolution of spinal instrumented technology leading to advances in the compassionate care of the spinal patient.

Figure 6A:
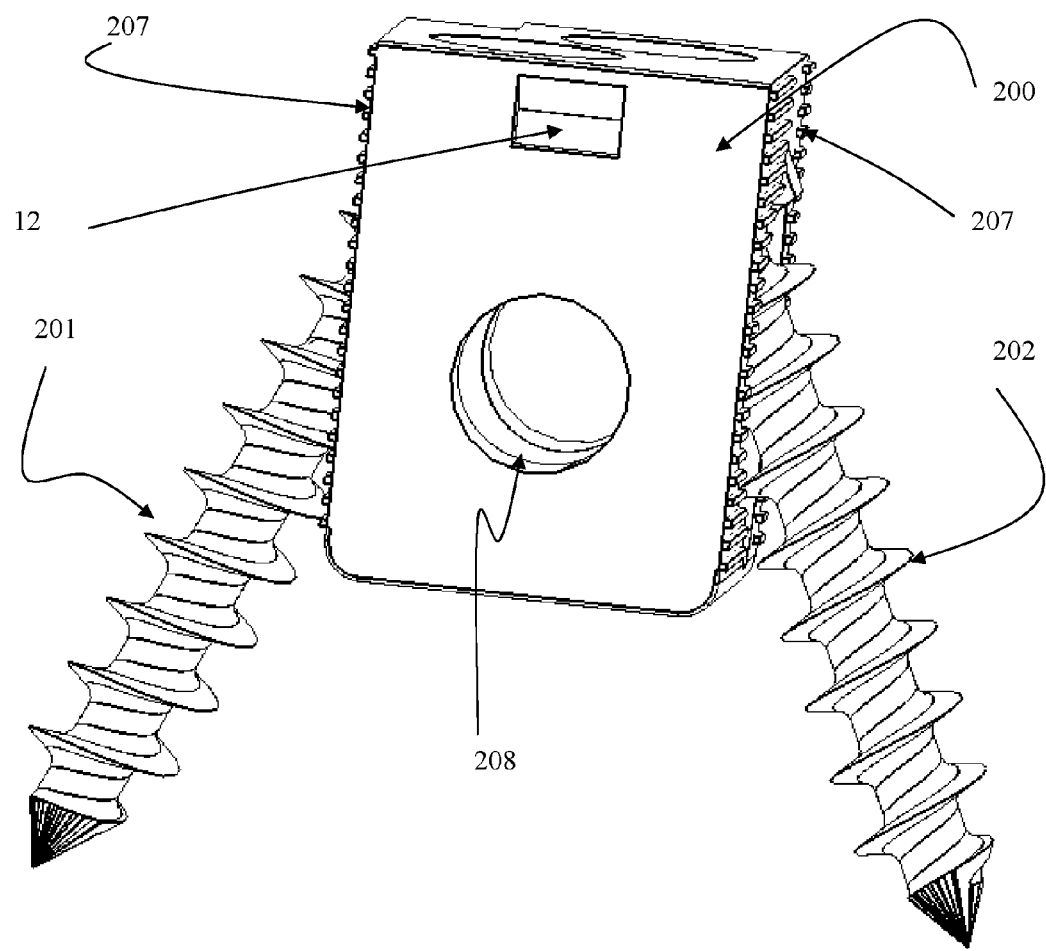
FIG. 6A illustrates a perspective view of an intervertebral cage construct according to an embodiment of the invention.
Figure 6B:
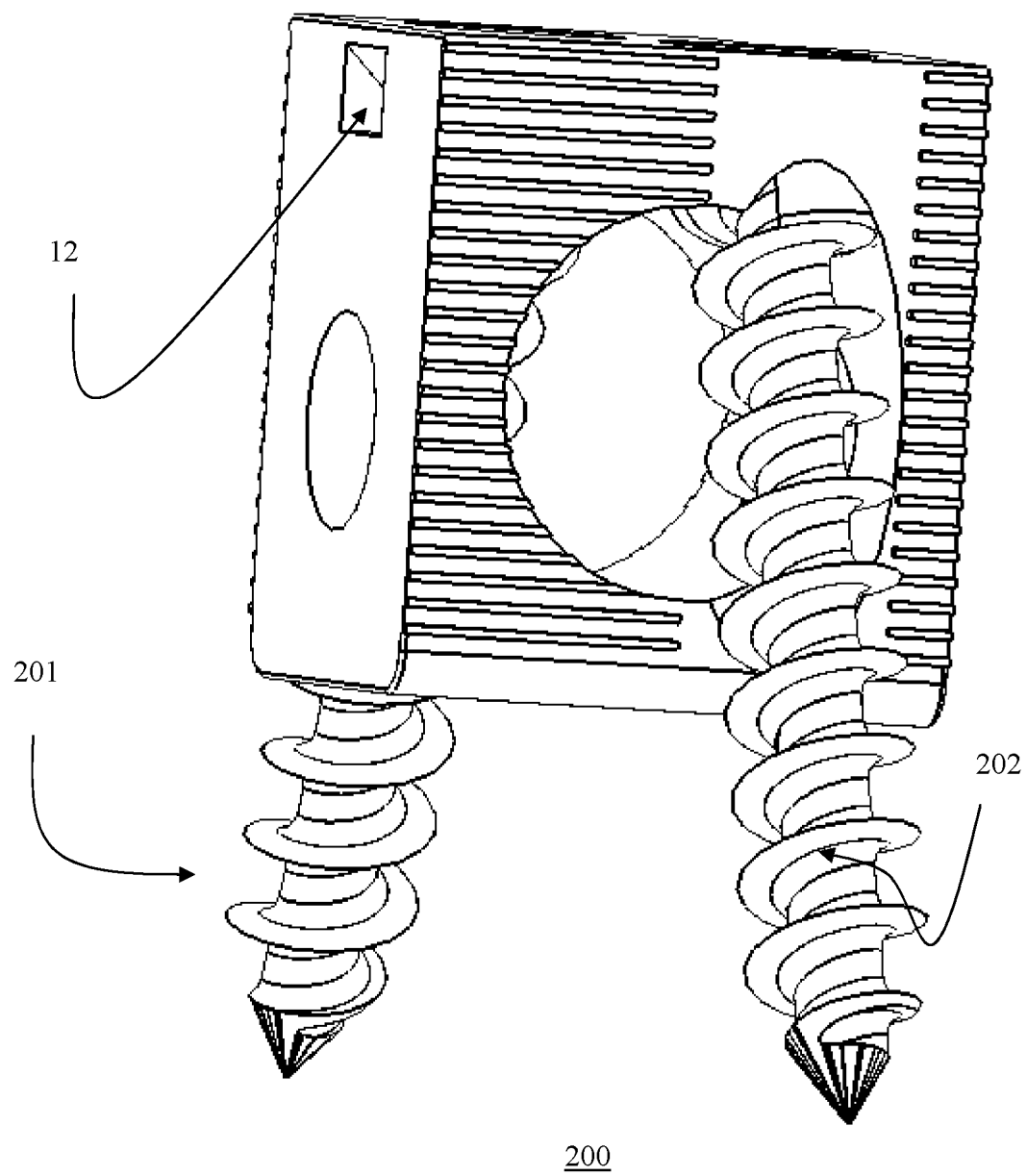
FIG. 6B illustrates another perspective view of an intervertebral cage construct according to an embodiment of the invention.
Figure 6C:
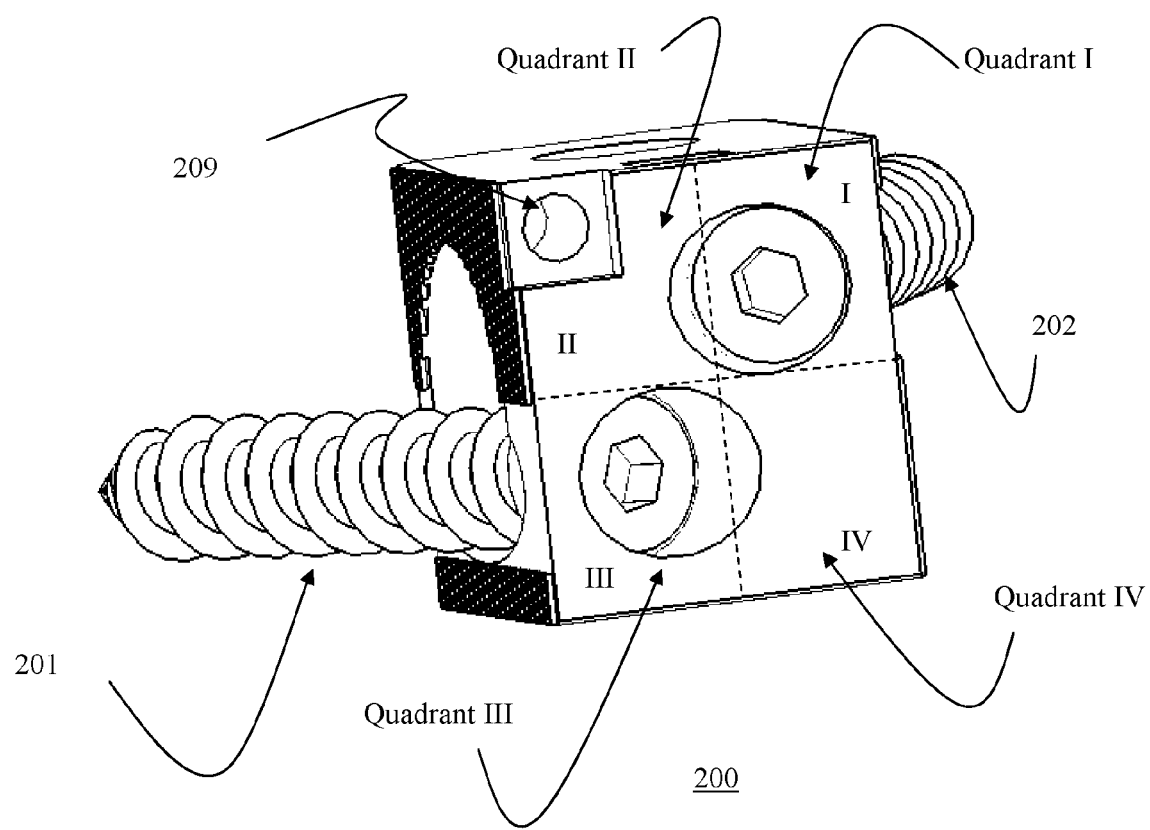
FIGS. 6C(i) and 6C(ii) illustrate top, perspective view of an intervertebral cage construct according to an embodiment of the invention.

FIGS. 6A, 6B, 6C(i), and 5C(ii) illustrate an exemplary embodiment of exemplary cage 200. These features are shown for example purposes, are not limited to the cage 200, and can be incorporated into any cage according to any of the embodiments described herein. As shown in FIGS. 6C(i) and 6C(ii), the screw guides can be positioned within four (4) quadrants I, II, III, IV.

For example, the intervertebral cage can include a wall having an entry opening of the first integral screw guide and an entry opening of the second integral screw guide, wherein the wall of the cage can include four quadrants delineated by a first axis and a second axis each lying in a plane of the wall, and the first axis is at a right angle with respect to the second axis, wherein the four quadrants include a first quadrant, a second quadrant, a third quadrant, and a fourth quadrant, wherein the first quadrant and the fourth quadrant are opposed to the second quadrant and the third quadrant with respect to the first axis, and the first quadrant and the second quadrant are opposed to the third quadrant and the fourth quadrant with respect to the second axis, wherein the first quadrant is diagonally opposed to the third quadrant, and the second quadrant is diagonally opposed to the fourth quadrant, and wherein one of a majority of an area of the entry opening of the first integral screw guide is in the first quadrant and a majority of an area of the entry opening of the second integral screw guide is in the third quadrant; and the majority of the area of the entry opening of the first integral screw guide is in the second quadrant and the majority of the area of the entry opening of the second integral screw guide is in the fourth quadrant.

In an embodiment, the intervertebral cage can include a wall having an entry opening of the first integral screw guide and an entry opening of the second integral screw guide, wherein the wall has four quadrants delineated by a first axis and a second axis each lying in a plane of the wall, and the first axis is at a right angle with respect to the second axis, wherein the four quadrants include a first quadrant, a second quadrant, a third quadrant, and a fourth quadrant, wherein the first quadrant and the fourth quadrant are opposed to the second quadrant and the third quadrant with respect to the first axis, and the first quadrant and the second quadrant are opposed to the third quadrant and the fourth quadrant with respect to the second axis, wherein the first quadrant is diagonally opposed to the third quadrant, and the second quadrant is diagonally opposed to the fourth quadrant, and wherein one of a center of the entry opening of the first integral screw guide is in the first quadrant and a center of the entry opening of the second integral screw guide is in the third quadrant; and the center of the entry opening of the first integral screw guide is in the second quadrant and the center of the entry opening of the second integral screw guide is in the fourth quadrant.

Figure 6D:
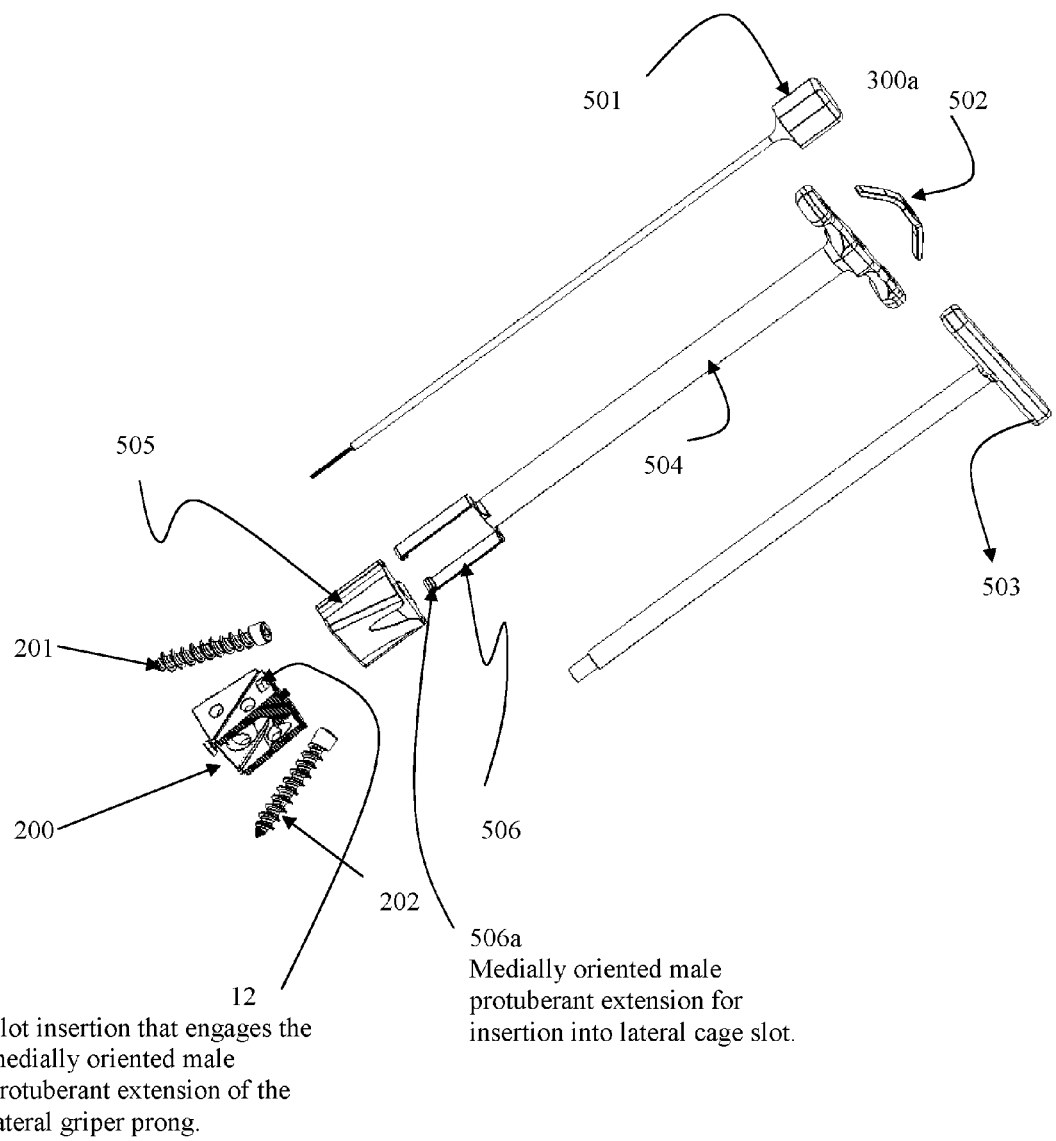
FIG. 6D illustrates a top, perspective, exploded view of a positioning tool/screw guide/box expander.

FIG. 6D illustrates an embodiment of an external drill/screw guide-box expander which assists in screw trajectory of the exemplary cage 200. The cage 200 can be a cage according to any of the embodiments described herein, or an expanding cage, in which case an expanding Allen key component can be used. The device can include, for example, an Allen key 501 (e.g., for an expandable cage), a spring 502, a handle 503, a gripper 504 having a gripper prong 506, which alternatively may include a male protuberance (e.g., a medially oriented mal protuberant extension for insertion into the lateral cage slot 12), and a screw guide 505.

Figure 6E:
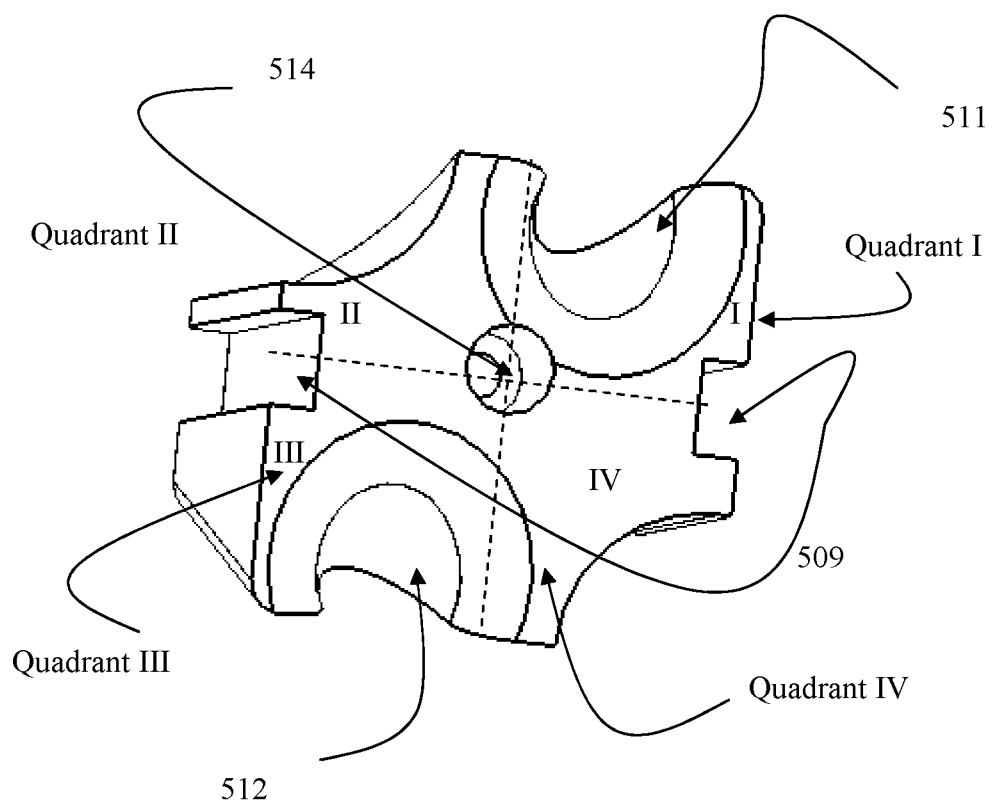
FIG. 6E illustrates a superior oblique perspective view of the positioning tool/drill guide/box expander component.

FIG. 6E illustrates a superior oblique view of the screw guide demonstrating insertions or grooves 509 for gripper prong 506 of the gripper 504 in FIG. 6D, built-in trajectory guides 511, 512 for insertions of screws, and an opening 514 for an Allen key, in instances in which an expandable cage is being used. In an embodiment, the Allen key may not be present when a non-adjustable cage is being used. In another embodiment, the Allen key may be present even when an adjustable cage is being used, such that the tool is universal to various types of cages.

The gripper 504 can include gripper prongs (e.g., medially oriented male protuberant extensions) 506 which insert into grooves 509 of the screw guide 505 and lateral slots (e.g., 12) of a cage, thereby perfectly aligning them.

Hence, according to the exemplary embodiments, a cage can be provided that has internal screw guides which have no gaps, and furthermore an insertion tool can be provided that has an external screw guide that further precisely guides the screws through the external tool screw guide, then into the internal implant screw guide guaranteeing the precise predetermined angulation of the screws. The combination the internal and external screw guides can create a long tunnel for a screw to enable a predetermined trajectory.

It is noted that the same trajectory can be provided by only with the internal box screw guides; however, one of ordinary skill will recognize that having the external screw guides as part of the tool further maintains the precise angle trajectory. The screw guide positions within the four (4) quadrants I, II, III, IV conform to the screw guide positions within the four (4) quadrants I, II, III, IV of the screw box.

With reference to the drawings, it will be understood that an embodiment of the indentations or recesses for the screw holes in any of the exemplary cages can be configured such that the screw heads will rest entirely within a peripheral side of a surface of the top portion of the cage (i.e., top surface). In this embodiment, the direction of the screw tunnel is from an anterior surface to a posterior of the top surface of the cage (i.e., the non-adjacent side).

In another embodiment, the indentations or recesses for the screw holes can be configured such that the screw heads will rest entirely within the peripheral side of the top surface of the cage. In this embodiment, the screw hole guide passes through the anterior-posterior axis of the top surface. The guides core circumference for the screw thread is surrounded by the lateral wall masses, and surrounded by mass from the front and rear surfaces (i.e., walls) of the cage.

In yet another embodiment, the indentations or recesses for the screw holes can be configured such that a recess for the screw holes are entirely within the peripheral side of the top surface of the box. In this embodiment, there is a through-hole for a screw which is counter-bored to keep the screw head within an outer surface boundary of the cage and in a direction to prevent the screw from avoiding the front or rear surfaces of the cage.

In yet another embodiment, the indentations or recesses for the screw holes can be configured such that a recess for the screw holes is entirely within the peripheral side of the front wall of the cage. In this embodiment, the tunnel for the screws is such that when the screw first enters, the screw will be surrounded by mass from the lateral sides and mass from the upper and lower sides of the wall. The screw will exit at the posterior end of the peripheral wall.

With reference to the drawings, it will be understood that an embodiment of the indentations or recesses for the screw holes can be configured such that a position of the screws is suitable for posterior lumbar screw holes.

For example, in an embodiment, the screw holes can be diagonal to each other along a transversal line. The transversal line can be defined as the line that would diagonally intersect and bypass the space between the recess for the screw holes.

In another embodiment, the screw holes can be diagonally opposed and lie on a congruent angle to each other from the intersecting transversal line.

In another embodiment, the recess for the screw holes can be diagonal and perpendicular to each other within the outer plane.

In another embodiment, the recess for the screw holes can be diagonal and symmetrically constrained within the outer wall of the cage.

While the foregoing disclosure shows illustrative embodiments of the invention, it should be noted that various changes and modifications could be made herein without departing from the scope of the invention as defined by the appended claims. The functions, steps and/or actions of the method claims in accordance with the embodiments of the invention described herein need not be performed in any particular order. Furthermore, although elements of the invention may be described or claimed in the singular, the plural is contemplated unless limitation to the singular is explicitly stated.

What is claimed is:

1. A universal, intervertebral combination bone fusion spacer and self-drilling screw apparatus for insertion into a disc space between a first vertebral body and a second vertebral body and fusion of the first vertebral body to the second vertebral body via biological bone fusion and screw fusion, the apparatus comprising:
    an intervertebral cage having a top wall, a bottom wall, a first side wall, and a second side wall defining a bone product placement cavity between the top wall and the bottom wall and between the first side wall and the second side wall, wherein the intervertebral cage defines a first vertebral body facing surface having a first set of ridges and a second vertebral body facing surface having a second set of ridges, wherein the first vertebral body facing surface is opposite of the second vertebral body facing surface and the bone product placement cavity extends through the intervertebral cage from the first vertebral body facing surface to the second vertebral body facing surface, wherein the top wall defines a top surface of the top wall and a bottom surface of the top wall each extending between the first vertebral body facing surface to the second vertebral body facing surface, wherein the intervertebral cage defines at least one locking mechanism engagement indentation extending into the top wall at an intersection of the top surface of the top wall and at least one of the first and second vertebral body facing surfaces, wherein the intervertebral cage further defines:
        a first internal screw guide extending through the top wall of the intervertebral cage and having a first predetermined angle, wherein the first internal screw guide extends from a first entrance opening formed in the top surface of the top wall to a first exit opening formed at least partially in the bottom surface of the top wall and at least partially in the first vertebral body facing surface; and
        a second internal screw guide extending through the top wall of the intervertebral cage and having a second predetermined angle, wherein the second internal screw guide extends from a second entrance opening formed in the top surface of the top wall to a first exit opening formed at least partially in the second vertebral body facing surface such that the second predetermined angle is different than the first predetermined angle;
    a first screw member disposed in the first internal screw guide at the first predetermined angle and extending past the first vertebral body facing surface;
    a second screw member disposed in the second internal screw guide at the second predetermined angle and extending past the second vertebral body facing surface; and
    a screw locking mechanism that secures both of the first screw member and the second screw member in the first internal screw guide and the second internal screw guide, respectively, wherein the screw locking mechanism comprises a base having a first screw blocking portion and a second screw blocking portion, wherein the screw locking mechanism comprises an engagement arm extending from the base into the locking mechanism engagement indentation of the intervertebral cage, wherein the engagement arm comprises a protuberance extending into the locking mechanism engagement indentation to resist removal of the screw locking mechanism from the intervertebral cage,
    wherein each of the first internal screw guide and the second internal screw guide is angled to orient the first screw member and the second screw bi-directionally in opposite directions,
    wherein the first screw member includes a first screw head and a first threaded body, wherein the first screw blocking portion of the base of the screw locking mechanism is positionable with respect to the intervertebral cage to partially block the first screw head to lock the first screw in the first internal screw guide,
    wherein the second screw member includes a second screw head and a second threaded body, wherein the second screw blocking portion of the base of the screw locking mechanism is positionable with respect to the intervertebral cage to partially block the second screw head to lock the second screw in the second internal screw guide.

2. The apparatus of claim 1, wherein the screw locking mechanism secures the first screw member in the first internal screw guide and the second screw member in the second internal screw guide.

3. The apparatus of claim 1, wherein the intervertebral cage includes a plurality of indentations including the locking mechanism engagement indentation positioned between the first and second screw guides; and
    wherein the screw locking mechanism comprises:
    a hemi bracket including:
        the base; and
        a plurality of arms including the engagement arm, the plurality of arms engaging the plurality of indentations to secure the hemi bracket to the intervertebral cage.

4. The apparatus of claim 1, wherein the locking mechanism engagement indentation is positioned between the first and second screw guides.

5. The apparatus of claim 3, wherein the hemi bracket covers and locks the first and second screws into the first and second internal screw guides and prevents the first and second screws from backing out of the first and second internal screw guides.

6. The apparatus of claim 1, further comprising:
a third screw member having a third tapered end and a third threaded body; and
wherein the cage further includes:
a third internal screw guide extending through the top wall of the intervertebral cage and having a third predetermined angle, wherein the third internal screw guide extends from a third entrance opening formed in the top surface of the top wall to a third exit opening formed at least partially in the second vertebral body facing surface.

7. The apparatus of claim 1, wherein each of the first integral screw guide and the second internal screw guide includes a descending narrowing screw guide that narrows in a direction extending from top to bottom.

8. The apparatus of claim 7, wherein the first screw member and the second screw member are disposed in each descending narrowing screw guide and countersunk on top of the intervertebral cage such that each descending narrowing screw guide hugs each respective one of the first screw member and the second screw member to provide a secondary locking mechanism for each of the first screw member and the second screw member that is independent of the screw locking mechanism.

9. The apparatus of claim 3, wherein each of the first internal screw guide and the second internal screw guide includes a descending narrowing screw guide that narrows in a direction extending from top to bottom, and
wherein the first screw member and the second screw member are disposed in each descending narrowing screw guide and countersunk on top of the intervertebral cage such that each descending narrowing screw guide hugs each respective one of the first screw member and the second screw member to provide a secondary locking mechanism for each of the first screw member and the second screw member that is independent of the screw locking mechanism.

10. The apparatus of claim claim 6, wherein each of the first, second, and third internal screw guides includes a descending narrowing screw guide that narrows in a direction extending from top to bottom, and
wherein the first, second, and third screw members are disposed in each respective descending narrowing screw guide and countersunk on top of the intervertebral cage such that each descending narrowing screw guide hugs each respective one of the each of the first, second, and third screw members to provide a secondary locking mechanism for each of the each of the first, second, third, and fourth screw members that is independent of the screw locking mechanism.

11. The apparatus of claim 1, wherein the screw locking mechanism includes an indentation adjacent to each of the first internal screw guide and the second integral screw guide.

12. The apparatus of claim 1, wherein the intervertebral cage further defines first and second tool engagement slots on the first and second side walls closer to the top surface of the top wall than to the bottom wall.

13. The apparatus of claim 1, wherein the screw locking mechanism further comprises a second engagement arm extending into a second locking mechanism engagement indentation of the intervertebral cage.

14. A system comprising the apparatus of claim 1 and an insertion tool having first and second gripper prongs sized and configured for gripping the intervertebral cage and having a screw guide that defines first and second angled trajectory guides for insertion of screws, wherein the first angled trajectory guide is aligned with the first internal screw guide when the first and second gripper prongs are engaged with the intervertebral cage so as guide the first screw member through the first angled trajectory guide of the screw guide of the insertion tool into the first internal screw guide of the intervertebral cage.

15. The system of claim 13, wherein the first and second angled trajectory guides are positioned between the first and second gripper prongs with respect to an axis of a handle of the insertion tool.

16. The apparatus of claim 1, wherein the intervertebral cage comprises means for receiving a prong of an implantation tool and wherein the screw locking mechanism comprises means for snapping into the intervertebral cage.

17. The apparatus of claim 1, wherein at least a portion of the base of the screw locking mechanism has a top base surface that is substantially planar and parallel to the top surface of the top wall of the intervertebral cage.

* * * * *

UNITED STATES PATENT AND TRADEMARK OFFICE
CERTIFICATE OF CORRECTION

Page 1 of 3

PATENT NO. : 10,098,678 B2
APPLICATION NO. : 15/397198
DATED : October 16, 2018
INVENTOR(S) : Nathan C. Moskowitz et al.

It is certified that error appears in the above-identified patent and that said Letters Patent is hereby corrected as shown below:

On the Title Page

Page 2, item (60), Column 1, Line 45 (Related U.S. Application Data): Delete "continuation" and insert -- continuation-in-part --, therefor.

Page 2, item (60), Column 1, Line 47 (Related U.S. Application Data): Delete "continuation" and insert -- continuation-in-part --, therefor.

In the Specification

Column 1-2, Line 8-67 (Column 1) 1-8 (Column 2): Delete "This application is a Continuation application, for which priority is claimed under 35 U.S.C. § 120, U.S. patent application Ser. No. 13/418,225, filed on Mar. 12, 2012, which is a Continuation-In-Part application, for which priority is claimed under 35 U.S.C. § 120, U.S. patent application Ser. No. 13/401,829, filed Feb. 21, 2012, Ser. No. 13/103,994, filed May 9, 2011, Ser. No. 13/084,543, filed Apr. 11, 2011, now U.S. Pat. No. 8,353,913, issued Jan. 15, 2013, Ser. No. 11/842,855, filed Aug. 21, 2007, now U.S. Pat. No. 7,942,903, issued May 17, 2011, Ser. No. 11/536,815, filed Sep. 29, 2006, now U.S. Pat. No. 7,846,188, issued Dec. 7, 2010, and Ser. No. 11/208,644, filed Aug. 23, 2005, now U.S. Pat. No. 7,704,279, issued Apr. 27, 2010, and which is a Divisional application, for which priority is claimed under 35 U.S.C. § 120, U.S. patent application Ser. No. 12/054,335, filed Mar. 24, 2008, now U.S. Pat. No. 7,972,363, issued Jul. 5, 2011, and Ser. No. 11/842,855, filed Aug. 21, 2007, now U.S. Pat. No. 7,942,903, issued May 17, 2011. This application claims the benefit of priority under 35 U.S.C. § 119(e) of U.S. Provisional Application 60/670,231, filed May 12, 2005, 61/451,582, filed Mar. 10, 2011, 61/451,579, filed Mar. 10, 2011, and 61/445,034, filed Feb. 21, 2011.
This application is a Continuation application, for which priority is claimed under 35 U.S.C. § 120, U.S. patent application Ser. No. 13/418,323, filed on Mar. 12, 2012, which is a Continuation-In-Part application, for which priority is claimed under 35 U.S.C. § 120, U.S. patent application Ser. No. 13/401,829, filed Feb. 21, 2012, Ser. No. 13/103,994, filed May 9, 2011, Ser. No. 13/084,543, filed Apr. 11, 2011, now U.S. Pat. No. 8,353,913, issued Jan. 15, 2013, Ser. No. 11/842,855, filed Aug. 21, 2007, now U.S. Pat. No. 7,942,903, issued May 17, 2011, Ser. No. 11/536,815, filed Sep. 29, 2006, Signed and Sealed this
Seventh Day of May, 2019

Andrei Iancu
*Director of the United States Patent and Trademark Office*

CERTIFICATE OF CORRECTION (continued)
U.S. Pat. No. 10,098,678 B2 now U.S. Pat. No. 7,846,188, issued Dec. 7, 2010, and Ser. No. 11/208,644, filed Aug. 23, 2005, now U.S. Pat. No. 7,704,279, issued Apr. 27, 2010, and which is a Divisional application, for which priority is claimed under 35 U.S.C. § 120, U.S. patent application Ser. No. 12/054,335, filed Mar. 24, 2008, now U.S. Pat. No. 7,972,363, issued Jul. 5, 2011, and Ser. No. 11/842,855, filed Aug. 21, 2007, now U.S. Pat. No. 7,942,903, issued May 17, 2011. This application claims the benefit of priority under 35 U.S.C. § 119(e) of U.S. Provisional Application 60/670,231, filed May 12, 2005, 61/451,582, filed Mar. 10, 2011, 61/451,579, filed Mar. 10, 2011, and 61/445,034, filed Feb. 21, 2011.

This application is a Continuation application, for which priority is claimed under 35 U.S.C. § 120, U.S. patent application Ser. No. 13/401,829, filed on Feb. 21, 2012, which is a Continuation-In-Part application, for which priority is claimed under 35 U.S.C. § 120, U.S. patent application Ser. No. 13/103,994, filed May 9, 2011, Ser. No. 13/084,543, filed Apr. 11, 2011, now U.S. Pat. No. 8,353,913, issued Jan. 15, 2013, Ser. No. 11/842,855, filed Aug. 21, 2007, now U.S. Pat. No. 7,942,903, issued May 17, 2011, Ser. No. 11/536,815, filed Sep. 29, 2006, now U.S. Pat. No. 7,846,188, issued Dec. 7, 2010, and Ser. No. 11/208,644, filed Aug. 23, 2005, now U.S. Pat. No. 7,704,279, issued Apr. 27, 2010, and which is a Divisional application, for which priority is claimed under 35 U.S.C. § 120, U.S. patent application Ser. No. 12/054,335, filed Mar. 24, 2008, now U.S. Pat. No. 7,972,363, issued Jul. 5, 2011, and Ser. No. 11/842,855, filed Aug. 21, 2007, now U.S. Pat. No. 7,942,903, issued May 17, 2011. This application claims the benefit of priority under 35 U.S.C. § 119(e) of U.S. Provisional Application 60/670,231, filed May 12, 2005, 61/451,582, filed Mar. 10, 2011, 61/451,579, filed Mar. 10, 2011, and 61/445,034, filed Feb. 21, 2011." and insert -- This application is a Continuation Application U.S. Patent Application Serial No. 13/418,335, filed on Mar. 12, 2012, which is a Continuation-In-Part of Application 13/103,994, filed May 9, 2011, now U.S. Patent No. 9,603,713, which is a Divisional of 12/054,335, filed Mar. 24, 2008, now U.S. Patent No. 7,972,363, which is a Continuation-In-Part of 11/842,855, filed Aug. 21, 2007, now U.S. Patent No. 7,942,903, which is a Continuation-In-Part of 11/536,815, filed Sep. 29, 2006, now U.S. Patent No. 7,846,188, which is a Continuation-In- Part of 11/208,644, filed Aug. 23, 2005, now U.S. Patent No. 7,704,279. Application 13/418,335 is a Continuation-In-Part of 13/084,543, filed Apr. 11, 2011, now U.S. Patent No. 8,353,913, which is a Divisional of 11,842,855, filed Aug. 21, 2007, now U.S. Patent No. 7,942,903. Application 13/418,335 claims the benefit of priority of 61/451,582, filed Mar. 10, 2011, 61/451,579, filed Mar. 10, 2011, and 61/445,034, filed Feb. 21, 2011 and is a Continuation-In-Part of 13/401,829, filed Feb. 21, 2012, now U.S. Patent No. 9,744,052. Application 11/208,644 claims benefit of 60/670,231, filed Apr. 12, 2005. Application 13/401,829 claims benefit of 61/445,034, filed Feb. 21, 2011.

This application is a Continuation of 13/418,323, filed Mar. 12, 2012, now U.S. Patent No. 9,814,601, which is a Continuation-In-Part of 13/103,994, filed May 9, 2011, now U.S. Patent No. 9,603,713, which is a Divisional of 12/054,335, filed Mar. 24, 2008, now U.S. Patent No. 7,972,363, which is a Continuation-In-Part of 11/842,855, filed Aug. 21, 2007, now U.S. Patent No. 7,942,903, which is a Continuation-In-Part of 11/536,815, filed Sep. 29, 2006, now U.S. Patent No. 7,846, 188, which is a Continuation-In-Part of 11/208,644, filed Aug. 23, 2005, now U.S. Patent No. 7,704,279. Application 13/418,323 is a Continuation-In-Part of 13/084,543, filed Apr. 11, 2011, now U.S. Patent No. 8,353,913, which is a Divisional of 11/842,855, filed Aug. 21, 2007, now U.S. Patent No. 7,942,903. Application 13/418,323 claims benefit of 61/451,582, filed Mar. 10, 2011 and claims benefit of 61/451,579, filed Mar. 10, 2011 and is a Continuation-In-Part of 13/401,829, filed Feb. 21, 2012, now U.S. Patent No. 9,744,052. Application 13/401,829 claims benefit of 61/445,034, filed Feb. 21, 2011. Application 15/397,198 is a Continuation-In-Part of 13/401,829, filed Feb. 21, 2012, now U.S. Patent No. 9,744,052, which is a Continuation-In-Part of 13/103,994, filed May 9, 2011, now U.S. Patent No.

CERTIFICATE OF CORRECTION (continued)
U.S. Pat. No. 10,098,678 B2

9,603,713, which is a Divisional of 12/054,335, filed Mar. 24, 2008, now U.S. Patent No. 7,972,363, which is a Continuation-In-Part 11/842,855, filed Aug. 21, 2007, now U.S. Patent No. 7,942,903, which is a Continuation-In-Part 11/536,815, filed Sep. 29, 2006, now U.S. Patent no. 7,846,188, which is a Continuation-In-Part of 11/208,644, filed Aug. 23, 2005, now U.S. Patent No. 7,704,279. Application 13/401,829 is a Continuation-In-Part of 13/084,543, filed Apr. 11, 2011, now U.S. Patent No. 8,353,913, which is a Divisional of 11/842,855, filed Aug. 21, 2007, now U.S. Patent No. 7,942,903. Application 13/401,829 claims benefit of 61/451,582, filed March 10, 2011, 61/451,579, filed Mar. 10, 2011, 61/445,034, filed February 21, 2011. --, therefor.

In the Claims

Column 23, Line 13: In Claim 7, delete "integral" and insert -- internal --, therefor.

Column 23, Line 38: In Claim 10, delete "claim claim" and insert -- claim --, therefor.

Column 24, Line 5: In Claim 10, delete "each of the each of the" and insert -- each of the --, therefor.

Column 24, Line 10: In Claim 11, delete "integral" and insert -- internal --, therefor.